(12) United States Patent
Schomberg

(10) Patent No.: US 6,582,120 B2
(45) Date of Patent: Jun. 24, 2003

(54) METHOD AND X-RAY DEVICE FOR THE ACQUISITION OF A SET OF PROJECTION IMAGES OF AN OBJECT TO BE EXAMINED

(75) Inventor: Hermann Schomberg, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/023,141
(22) Filed: Dec. 18, 2001
(65) Prior Publication Data
US 2002/0168053 A1 Nov. 14, 2002

(30) Foreign Application Priority Data

Dec. 20, 2000 (DE) .......................... 100 63 442

(51) Int. Cl.[7] .............. H05G 1/02; A61B 6/03
(52) U.S. Cl. .............. 378/197; 378/196; 378/185; 378/15
(58) Field of Search .............. 378/197, 196, 378/195, 198, 15

(56) References Cited

U.S. PATENT DOCUMENTS

| | | | | |
|---|---|---|---|---|
| 5,038,371 A | * | 8/1991 | Janssen et al. .............. 378/197 |
| 5,073,917 A | * | 12/1991 | Van Endschot et al. .... 378/197 |
| 5,095,501 A | * | 3/1992 | Kobayashi .................. 378/195 |
| 6,092,928 A | * | 7/2000 | Mattson et al. ............. 378/197 |
| 6,438,194 B2 | * | 8/2002 | Grass et al. .................... 378/4 |

* cited by examiner

Primary Examiner—Drew A. Dunn
(74) Attorney, Agent, or Firm—John Vodopia

(57) ABSTRACT

A method for the acquisition of a set of projection images for the reconstruction of a three-dimensional image data set of an object to be examined that is arranged in an examination zone, said acquisition being performed by way of an X-ray device that includes an X-ray source and an X-ray detector, said X-ray source being guided along a trajectory around the examination zone, said trajectory being situated essentially on a spherical surface, in order to acquire the projection images. In accordance with the invention the trajectory is configured in such a manner that the X-ray source can continuously follow the trajectory in order to acquire the set of projection images and that not all points of the trajectory are situated in a common plane. This enables fast acquisition of a set of projection data that enables an exact reconstruction of the object to be examined. The invention also relates to a corresponding X-ray device.

17 Claims, 23 Drawing Sheets

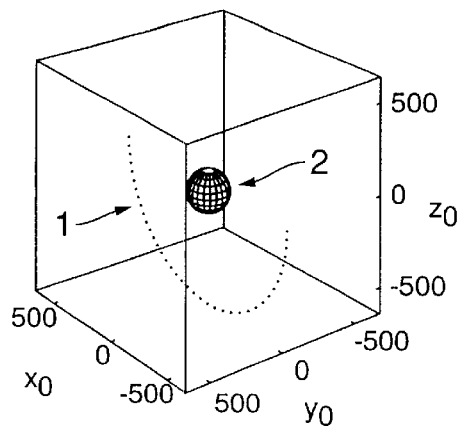
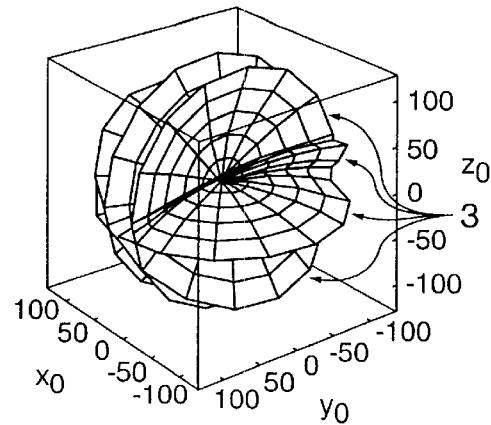
FIG.2a          FIG.2b
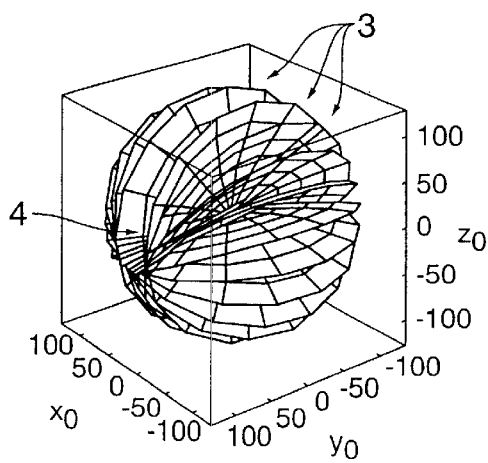
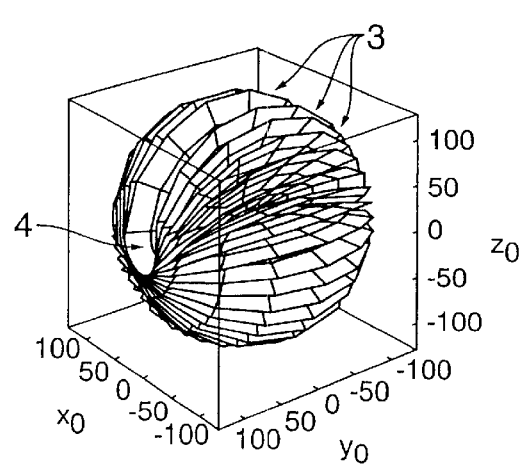
FIG.2c          FIG.2d

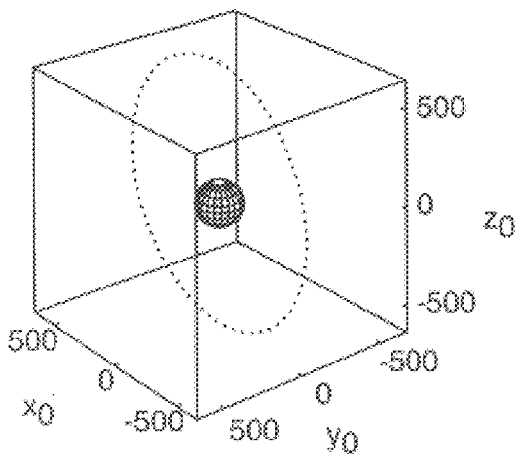 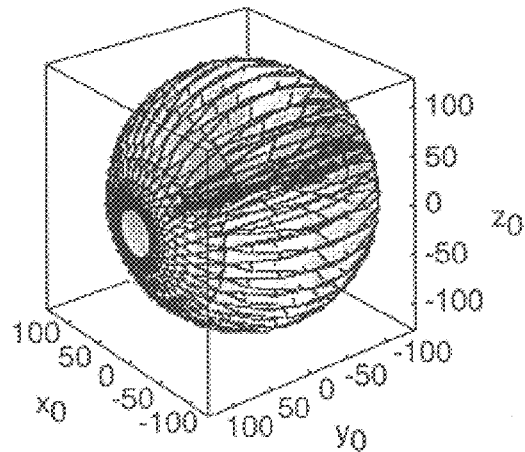
FIG.3a  FIG.3b
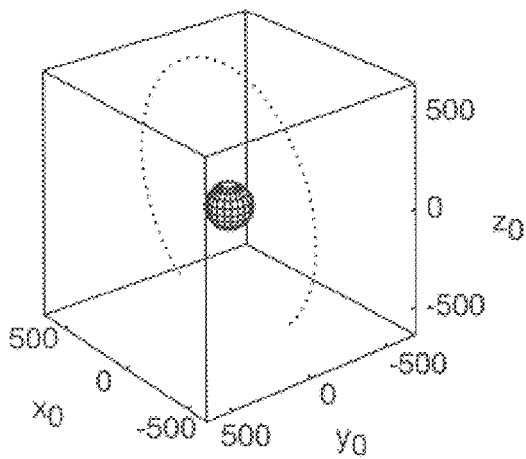 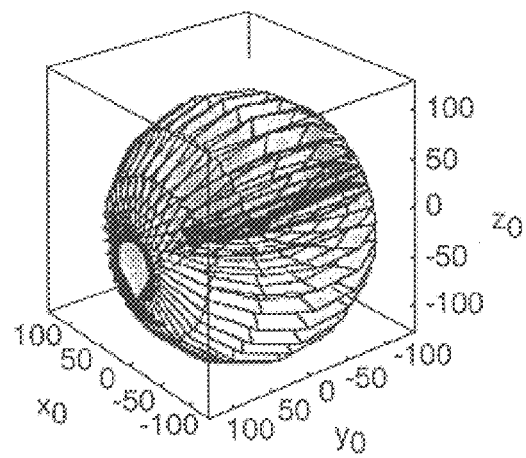
FIG.3c  FIG.3d

| Trajektorie aus | Rotationswinkel für 1. Ausführungsbeispiel | Rotationswinkel für 2. Ausführungsbeispiel |
|---|---|---|
| Fig. 10a | $\alpha_1(s)$ 0<br>$\alpha_2(s)$ $-\pi/2 + 2\pi s$<br>$\alpha_3(s)$ $3/4(\pi/4 - \pi s/2)$ | $\alpha_1(s)$ $\pi/2$<br>$\alpha_2(s)$ $-\pi/2 + (1/2 - s)\pi/3$<br>$\alpha_3(s)$ $-2\pi s$ |
| Fig. 11a | $\alpha_1(s)$ 0<br>$\alpha_2(s)$ $-\pi/2 + 2\pi s$<br>$\alpha_3(s)$ $\cos[\pi s]\pi/12$ | $\alpha_1(s)$ $\pi/2$<br>$\alpha_2(s)$ $-\pi/2 + \cos[\pi s]\pi/10$<br>$\alpha_3(s)$ $-\pi s$ |
| Fig. 12a | $\alpha_1(s)$ 0<br>$\alpha_2(s)$ $-\pi/2 + 2\pi s \cdot 3/4$<br>$\alpha_3(s)$ $3/4(\pi/4 - \pi s/2)$ | $\alpha_1(s)$ $\pi/2$<br>$\alpha_2(s)$ $-\pi/2 + (3/8 - s \cdot 3/4)\pi$<br>$\alpha_3(s)$ $-\pi/4 - 3\pi s/2$ |
| Fig. 13a | $\alpha_1(s)$ 0<br>$\alpha_2(s)$ $\pi/2 - (135/360)\pi - (225/360)2\pi \sin^2[\pi s/2]$<br>$\alpha_3(s)$ $\sin[2\pi s]/2$ | |
| Fig. 14a | $\alpha_1(s)$ 0<br>$\alpha_2(s)$ $-\pi/4 + 2\pi s$<br>$\alpha_3(s)$ $-\cos[4\pi s]/4$ | $\alpha_1(s)$ $\pi/2$<br>$\alpha_2(s)$ $-\pi/2 - \sin[2\pi s]/2$<br>$\alpha_3(s)$ $-\pi s$ |
| Fig. 15a | $\alpha_1(s)$ 0<br>$\alpha_2(s)$ $2\pi s$<br>$\alpha_3(s)$ $-\text{sign}[s-1/2]\sin^4[2\pi s]/2$ | $\alpha_1(s)$ $\pi/2$<br>$\alpha_2(s)$ $-\pi/2 + \text{sign}[s-1/2]\sin^3[2\pi s]/2$<br>$\alpha_3(s)$ $-\pi/2 - \pi s$ |
| Fig. 16a | $\alpha_1(s)$ 0<br>$\alpha_2(s)$ $-\pi/2 + 4\pi s$<br>$\alpha_3(s)$ $\cos[2\pi s]/12$ | $\alpha_1(s)$ $\pi/2$<br>$\alpha_2(s)$ $-\pi/2 + \cos[2\pi s]\pi/10$<br>$\alpha_3(s)$ $-4\pi s$ |
| Fig. 17a | $\alpha_1(s)$ 0<br>$\alpha_2(s)$ $4\pi s$<br>$\alpha_3(s)$ $-\text{sign}[s-1/2]\sin^4[4\pi s]/2$ | $\alpha_1(s)$ $\pi/2$<br>$\alpha_2(s)$ $-\pi/2 + \text{sign}[s-1/2]\sin^3[4\pi s]/2$<br>$\alpha_3(s)$ $-\pi/2 - 4\pi s$ |
| Fig. 18a | $\alpha_1(s)$ 0<br>$\alpha_2(s)$ $\pi/2 - 3\pi/8 - 5\pi \sin^2[\pi s]/4$<br>$\alpha_3(s)$ $\sin[4\pi s]/4$ | |
| Fig. 19a | $\alpha_1(s)$ 0<br>$\alpha_2(s)$ $-\pi/2 + 24\pi s$<br>$\alpha_3(s)$ $\cos \pi s/10$ | |

FIG. 9

METHOD AND X-RAY DEVICE FOR THE ACQUISITION OF A SET OF PROJECTION IMAGES OF AN OBJECT TO BE EXAMINED

BACKGROUND

1. Field of the Invention

The invention relates to a method for the acquisition of a set of projection images for the reconstruction of a three-dimensional image data set of an object to be examined that is arranged in an examination zone, said acquisition being performed by means of an X-ray device that includes an X-ray source and an X-ray detector, the X-ray source being displaced along a trajectory around the examination zone, said trajectory being situated essentially on a spherical surface, in order to acquire the projection images. The invention also relates to an X-ray device that is suitable for carrying out such a method.

2. Description of Related Art

The so-called cone beam-computed tomography technique aims to reconstruct a three-dimensional image of an object to be examined from a set of cone beam projections of this object. An examination device that is provided with a punctiform X-ray source as well as with a flat X-ray detector is used for the measurement of the cone beam projections. The object is situated between the source and the detector. While the object remains stationary, the source and the detector are moved around the object; during this displacement cone beam projections are measured at short intervals in space or in time. The source and the detector are usually rigidly coupled to one another and the connecting line between the source and the center of the detector always passes through a defined point that is referred to as the isocenter. The trajectory of the source also determines the trajectory of the detector in such a case. Moreover, when small mechanical inaccuracies are ignored, the trajectory of the source is situated on the surface of a sphere whose center constitutes the isocenter. The trajectory of the source can be described by an image a: $[s_-,s_+] \to R^3$, where s is a real parameter and a(s) denotes the position vector of the trajectory relative to a Cartesian system of co-ordinates, the center of which is situated at the isocenter. The reconstructed image of the object represents the spatial distribution of the X-ray attenuation coefficient in the examination zone. The image is calculated from the measured set of cone beam projections by means of a computer and a reconstruction algorithm.

Numerous conditions must be satisfied so as to enable an exact reconstruction of the X-ray attenuation coefficient. One of these conditions is indicated and substantiated, for example, by P. Grangeat in "Mathematical framework of cone beam 3D reconstruction via the first derivative of the Radon transform", in G. T. Herman, A. K. Louis and F. Natterer, Mathematical Methods in Tomography, Vol. 1497 of the Lecture Notes in Mathematics, Springer Verlag, 1991, pp. 66 to 97. This condition is known as the completeness condition which stipulates that each plane that intersects the examination zone should also intersect the trajectory of the X-ray source. A trajectory that satisfies the completeness condition in relation to an examination zone will be deemed to be complete in relation to this examination zone hereinafter.

In the case of an isocentric examination device the examination zone is preferably an isocentric sphere $B(r_{max})$ having the radius $r_{max}$. The completeness condition can also be formulated differently for a spherical examination zone. In order to derive such an alternative formulation, first the set of all planes that intersect an arbitrary but fixed point a(s) of the trajectory as well as the sphere $B(r_{max})$ is considered. Each of these planes is unambiguously characterized by its normal vector in relation to the center of the sphere $B(r_{max})$, that is, the isocenter. Simple geometrical considerations that can be understood on the basis of FIG. 1 demonstrate that such normal vectors form a spherical cap $U(a(s),r_{max})$ where the associated sphere has the center a(s)/2 and the radius $|a(s)/2|$. When the parameter s is varied, and hence also the point a(s), the spherical cap $U(a(s),r_{max})$ is also varied. When the parameter s traverses the interval $[s_-,s_+]$, a corresponding number of spherical caps is obtained. From a construction point of view this number of spherical caps contains exactly those normal vectors that are associated with those planes that intersect the trajectory as well as the spherical examination zone $B(r_{max})$. Thus, in order to satisfy the completeness condition, this number of spherical caps must fill the sphere $B(r_{max})$ completely. This is because if a void were present, the planes that are associated with the normal vectors in this void would intersect the examination zone but not the trajectory.

For a given trajectory and a given sphere $B(r_{max})$, a dense sub-set of the set comprising all spherical caps can be calculated and graphically represented by means of a computer and a suitable computer program, after which it can be visually checked whether these spherical caps fill the sphere $B(r_{max})$ without voids or not. As opposed to the first formulation of the completeness condition, the second formulation thus enables a visual test as to whether or not a given trajectory is complete in relation to a given sphere $B(r_{max})$.

It is to be noted that a plane trajectory, that is, a trajectory that is situated completely within one plane, cannot be complete. This is because all planes that extend parallel to the plane of the trajectory and differ therefrom do not intersect the trajectory. Notably a circular trajectory or a segment thereof cannot be complete. However, there are trajectories that are composed of plane segments and are complete. These trajectories include, for example two circles that have the same diameter and the same center and whose axes enclose an angle that is large enough relative to one another.

When the trajectory of the X-ray source is not complete, it can nevertheless be attempted to reconstruct an image of the object to be examined. Generally speaking, however, shortcomings in the image quality will have to be accepted in such a case.

The examination device, however, must also be capable of realizing the trajectory of the X-ray source. In medical applications the object to be examined is a part of a patient who is accommodated on an examination table and it must be ensured that the X-ray source and the X-ray detector do not collide with the object to be examined or with the support for the object.

The Philips INTEGRIS V5000 is an examination device in conformity with the state of the art. This examination device has a C-arm, one end of which supports an X-ray source while an X-ray detector is mounted at its other end. The object to be examined is arranged between the X-ray source and the X-ray detector. The C-arm is supported by a circular rail, so that it can be rotated about its axis. This so-called C-arm axis extends perpendicularly to the plane that contains the C-arm. The support for the C-arm is connected, via a pivot joint, to a so-called L-arm which itself is connected, via a further pivot joint, to a suspension device that is mounted on the ceiling. This suspension device can be displaced rectilinearly and horizontally. The three axes mentioned always intersect one another in one point, that is, the isocenter. An electric motor provides the controllable rotation of the X-ray source and the X-ray detector about the C-arm axis. Rotations about the other two axes are assisted by servomotors, but cannot be controlled. The acquisition of a set of cone beam projections of the object to be examined takes place during a revolution of the C-arm about the C-arm axis. Because of the absence of control, rotations about the other two axes are not possible during the acquisition of cone beam projections in the INTEGRIS V5000. The rotation of the C-arm about its C-arm axis leads to a semicircular trajectory of the X-ray source. As has already been stated, such a trajectory is not complete.

A complete trajectory could in principle be composed from a plurality of semi-circles. The C-arm would then be positioned anew between the sub-examinations. However, that would be a time-consuming operation. For applications concerning the imaging of blood vessels, necessitating the administration of X-ray contrast media, moreover, the quantity of contrast medium to be administered would have to be increased.

SUMMARY OF THE INVENTION

It is an object of the present invention to provide a suitable method for the acquisition of a complete set of cone beam projections of an object to be examined that is arranged in an examination zone. It is also an object of the present invention to provide an X-ray device that is suitable for carrying out such a method.

This object is achieved by means of a method as disclosed in claim 1 and by means of an X-ray device as disclosed in claim 11, respectively. In accordance with the invention it is proposed to configure the trajectory in such a manner that the X-ray source can continuously follow the trajectory in order to acquire the set of projection images and that not all points of the trajectory are situated in a common plane.

In accordance with the first completeness condition, each plane that intersects the object to be examined must contain a point of the trajectory. When the trajectory is situated completely within a plane that intersects the object to be imaged, this trajectory does not satisfy the completeness condition. This is because each plane that is oriented parallel to the plane of the trajectory and intersects the object to be examined does not contain a point of the trajectory. Therefore, each trajectory that satisfies the completeness condition must be a three-dimensional curve, which means that it may not be situated in one plane.

Granted, the known trajectory that consists of two orthogonal circles is not situated in one plane and it also satisfies the completeness condition. However, it is configured in such a manner that the X-ray source is first rotated 360° about a first axis of rotation and subsequently through 360° about a second axis of rotation that extends perpendicularly to the first axis of rotation. Therefore, after a rotation about the first axis of rotation the X-ray source must be stopped and subsequently rotated about the second axis of rotation. Consequently, the trajectory cannot be followed continuously. In accordance with the invention, however, the X-ray source can be moved along a three-dimensional trajectory without having to be stopped. Consequently, the trajectory in accordance with the invention enables the acquisition of a complete set of projection images for a 3D image data set, that is, in a reliable and fast manner and in one operation. This contributes to the reconstruction of 3D images being essentially free from artefacts and inaccuracies.

In conformity with a preferred version of the present invention the trajectory is configured in such a manner that each plane that intersects the examination zone comprises at least one point of the trajectory. The completeness condition for the examination zone is thus satisfied, enabling accurate imaging of an object to be examined that is situated in the examination zone.

According to a preferred version of the present invention the trajectory forms a closed curve. A closed curve is characterized by the fact that after a finite time interval the X-ray source will return to its starting position when it is moved along the trajectory. It is thus possible to move the X-ray source several times along the trajectory around the object to be examined during the acquisition of projection images. Such a possibility is advantageous for the imaging of periodically moving organs such as the beating heart.

Preferably, the trajectory in accordance with the invention is a curve that is twice differentiable. When the time t at which the X-ray source is in the position a(t) of the trajectory is chosen as the curve parameter, the speed of the X-ray source will be given by the first derivative of the curve in time at any instant. Because the curve is twice differentiable, the first derivative exists. Furthermore, the first derivative is continuous because the curve is twice differentiable. The position of the X-ray source along the trajectory thus changes continuously as a function of time. Therefore, such a curve can be continuously followed by an X-ray source. In the case of an abrupt (meaning a discontinuous) change of the position of the X-ray source, however, it would be necessary to stop the X-ray source in such a location of abrupt change in order to follow the trajectory. Preferably, a trajectory in accordance with the invention is even chosen to be a curve that is continuously twice differentiable, notably with large radii of curvature. The accelerations occurring during the realization of the trajectory are thus kept small.

In accordance with the invention cone beam projections are preferably acquired as projection images.

The X-ray device in accordance with the invention is configured in such a manner that the X-ray source can continuously follow the trajectory in order to acquire the set of projection images and that not all points of the trajectory are situated in a common plane.

Preferably, the X-ray device in accordance with the invention is a C-arm system that includes a C-arm, the X-ray source being mounted at one end of said arm whereas the X-ray detector is connected to its other end. A C-arm enables the object to be examined to be arranged between the source and the detector. When the X-ray source is displaced along the trajectory, the X-ray detector performs a corresponding movement. The movement of the X-ray source around the object to be examined can be realized simply by movement of the C-arm.

The X-ray device is preferably constructed in such a manner that the C-arm is rotatable about a C-arm axis while at the same time the C-arm mount is rotatable about a propeller axis. The propeller axis and the C-arm axis extend perpendicularly to one another and have a common point of intersection, that is, the so-called isocenter. The straight connecting line between the focal spot of the X-ray source and the center of the detector also passes through the isocenter. The described arrangement of axes of rotation enables the X-ray source to be rotated on a spherical surface around the isocenter during a rotation around one of the axes of rotation. The object to be examined is arranged in the vicinity of the isocenter in order to acquire a 3D image data set. The propeller axis and the C-arm are situated essentially in a common plane. Upon rotation of the C-arm about the propeller axis, the sections of the C-arm whereto the X-ray source and the X-ray detector are attached are rotated about a common axis like the blades of a propeller. The rotation around the propeller axis may then amount to more than 360° or a multiple thereof.

In a preferred embodiment the propeller axis remains the same during a rotation of the C-arm about the C-arm axis.

A practical embodiment of an X-ray device in accordance with the invention is provided with a first mount for the X-ray source and the X-ray detector. Furthermore, this mount is rotatable about a first axis and connected to a second mount. The second mount is rotatable about a second axis and connected to a third mount. The third mount is connected, either rigidly or rotatably, to the building or is rotatably or slideably connected to a chain of one or more further mounts which are successively connected to one another by way of pivot joints and ultimately to the building. The first and the second axis intersect in one point. When the third mount is rotatably connected to the building or to a fourth mount, this third axis also intersects the point of intersection of the first two axes. The movements about the two first axes of rotation take place motorically and in a controlled manner. If present, the fourth and all further mounts serve to position the point of intersection of the first two axes in the vicinity of the object to be examined.

The above X-ray device is preferably configured in such a manner that the first axis mount is a C-arm whose ends support the X-ray source and the X-ray detector, respectively. The second mount supports said C-arm by means of a circularly bent rail, so that the C-arm can be rotated about the first axis which will be referred to hereinafter as the C-arm axis. The rotation about the second axis results in a propeller-like motion of the C-arm about the propeller axis. The C-arm axis and the propeller axis extend perpendicularly to one another and have a common point of intersection, being the so-called isocenter. The straight connecting line between the focal spot of the X-ray tube and the center of the detector also extends through the isocenter. The X-ray source is moved by rotating the C-arm and its C-arm axis and the mount of the C-arm about the propeller axis. Both rotations are required for a complete trajectory. The configuration of the axes of rotation ensures that the trajectory of the X-ray source is situated when ignoring small mechanical inaccuracies) on the surface of a sphere that is centered relative to the isocenter. The object to be examined is arranged in the vicinity of the isocenter.

The first mount can again be constructed so as to be arc-shaped but is connected to the second mount via a pivot joint. The third mount supports the second mount by way of a circularly bent rail, thus enabling a rotary movement. In comparison with the first embodiment the order of the propeller axis and the C-arm axis is reversed.

Further versions of the method in accordance with the invention and further embodiments of the device in accordance with the invention are disclosed in the dependent claims. It is to be noted that the X-ray device in accordance with the invention may be elaborated in the same way or in a similar way as the method in accordance with the invention as disclosed in the claims that relate directly or indirectly to claim 1.

BRIEF DESCRIPTION OF THE DRAWINGS

Preferred embodiments of the present invention will be described in detail hereinafter with reference to the accompanying Figures. Therein:

FIGS. 2a to 2d show a semi-circular trajectory in conformity with the present state of the art, together with the associated spherical caps of the trajectory, FIGS. 3a, 3b show a circular trajectory in conformity with the present state of the art, together with the associated spherical caps of the trajectory, FIGS. 3c, 3d show a trajectory that represents a ¾ circle in conformity with the state of the art, together with the associated spherical caps of the trajectory, FIG. 9 shows a table that contains the angle functions $\theta_1$, $\theta_2$, $\theta_3$ of different trajectories for the first embodiment of the X-ray device (left-hand column) and those for the second embodiment of the X-ray device (right-hand column)

DETAILED DESCRIPTION

Figure 1:
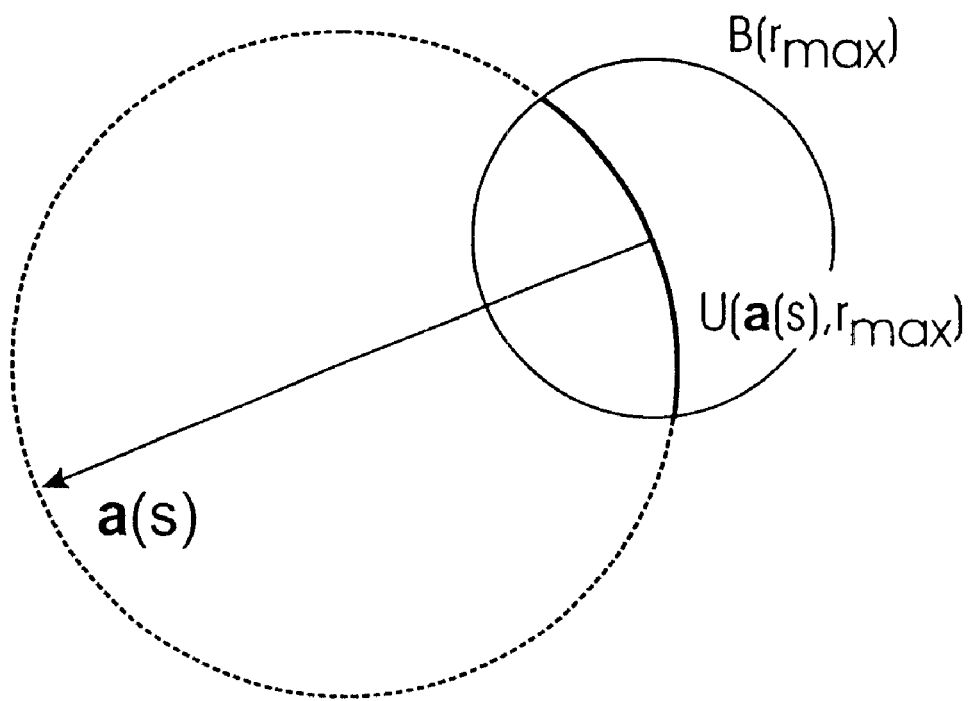
FIG. 1 shows the construction of a spherical cap for a point of a trajectory.

FIG. 2a shows a known, semi-circular trajectory 1 as well as the spherical examination zone 2. The FIGS. 2b to 2d illustrate the filling of the sphere 2 with spherical caps 3. FIG. 2b shows four spherical caps 3 while FIG. 2c shows 12 spherical caps 3 and FIG. 2d shows 19 spherical caps 3. The trajectory points that are associated with the spherical caps were each time distributed uniformly along the trajectory. The FIGS. 2b to 2d show that a semi-circular trajectory 1 is not complete, because it appears that a wedge-shaped zone 4 of the sphere 2 to be filled is void of spherical caps 3.

The FIGS. 3a and 3c show two trajectories that are also known. FIG. 3a shows a circular trajectory. FIG. 3b shows 36 spherical caps of the trajectory that is shown in FIG. 3a. It can be seen that a zone of the sphere that is to be filled remains void of spherical caps. This zone forms a double conical region. FIG. 3c shows a trajectory that corresponds to a ¾ circle. The 28 spherical caps for the ¾ circle that are shown in FIG. 3d cannot cover the described, double conical region. Therefore, the trajectories that are shown in the FIGS. 3a and 3c are not complete.

Figure 4A:
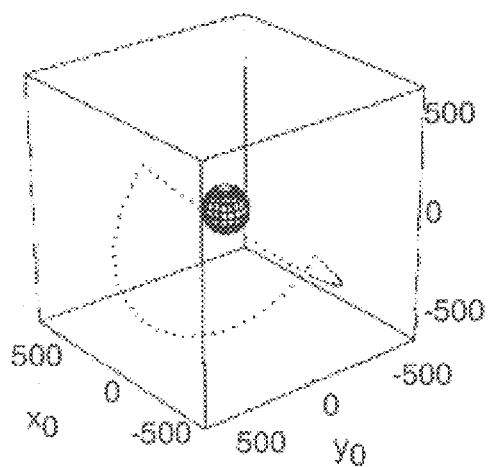
FIGS. 4a, 4b show a trajectory that consists of two mutually orthogonal semi-circles, together with the associated spherical caps of the trajectory.
Figure 4B:
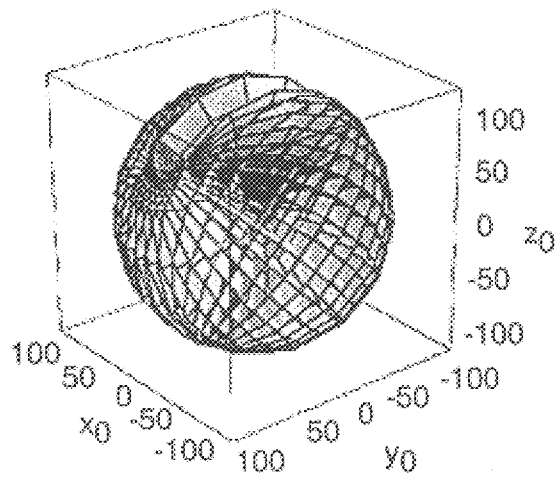
Figure 4C:
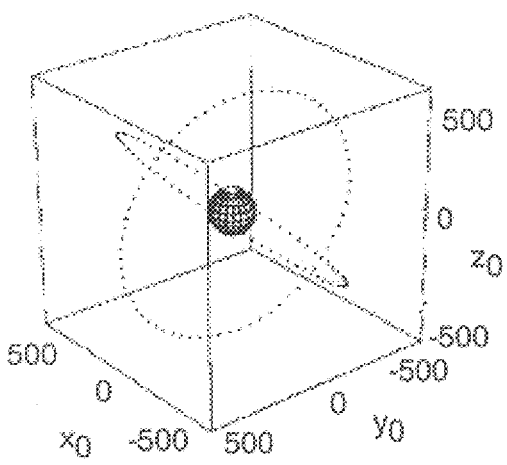
FIGS. 4c, 4d show a trajectory that consists of two orthogonal circles in accordance with the present state of the art, together with the associated spherical caps of the trajectory.
Figure 4D:
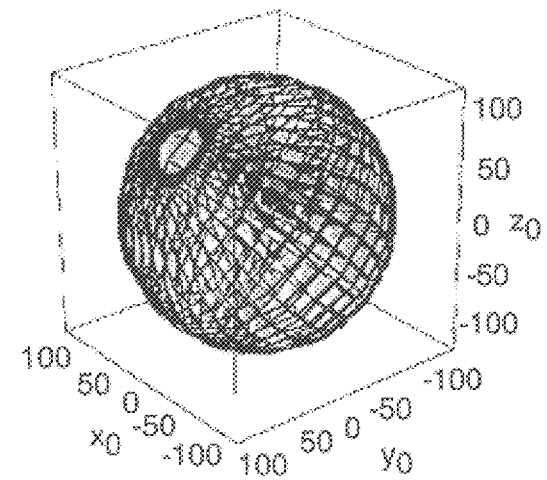

The FIGS. 4a and 4c show further known trajectories. FIG. 4a shows a trajectory that represents two orthogonal semi-circles. FIG. 4b shows 36 spherical caps for the trajectory in FIG. 4a. It can again be seen that this trajectory is not complete. FIG. 4c shows a trajectory that represents two orthogonal circles. FIG. 4d shows 72 spherical caps for the trajectory of FIG. 4c. As opposed to the previous examples, this trajectory is complete.

Figure 5:
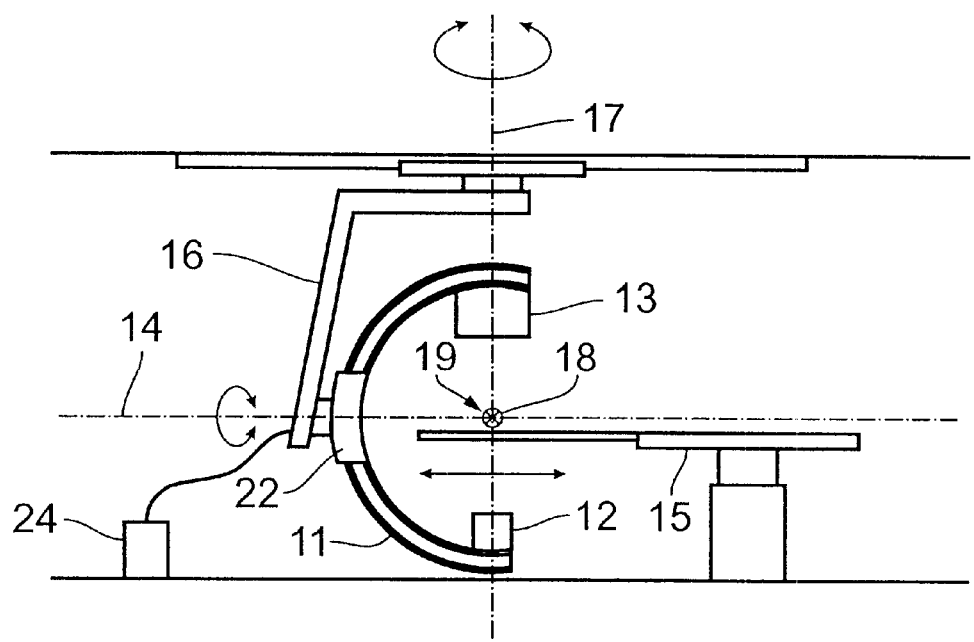
FIG. 5 is a side elevation of a first embodiment of an X-ray device in accordance with the invention.

FIG. 5 is a diagrammatic side elevation of a first embodiment of the X-ray device in accordance with the present invention. An X-ray source 12 and an X-ray detector 13 are mounted at opposite ends of the C-arm 11. The C-arm is journaled so as to be rotatable about a propeller axis 14 and a C-arm axis 19, that is by way of a C-arm mount 22. The C-arm axis 19 in this Figure is oriented perpendicularly to the plane of drawing and passes through an isocenter 18. A straight connecting line between the focal spot or center of the X-ray source 12 and the center of the X-ray detector 13 intersects the propeller axis 14 and the C-arm axis 19 at the isocenter 18. The C-arm 1 is journaled, by way of an L-arm 16, so as to be rotatable about an L-arm axis 17. The L-arm axis 17 intersects the propeller axis 14 and the C-arm axis 19 at the isocenter 18. The location and the orientation of the L-arm axis 17 and of the straight connecting line between the X-ray detector 13 and the X-ray source 12 correspond to one another in the basic position shown. A control unit 24 is provided for the control of the X-ray device.

As opposed to the X-ray device INTEGRIS V5000, the C-arm 11 with the X-ray detector 13 and the X-ray source 12 can be rotated about the C-arm axis 19 while at the same time the C-arm mount 22 is rotated about the propeller axis 14 and projection images of the object to be examined are acquired. Both rotary movements are performed by means of a motor and in a controlled fashion. The X-ray source 12 can thus be moved along a specified trajectory around the object to be examined at the area of the isocenter 18.

Figure 6:
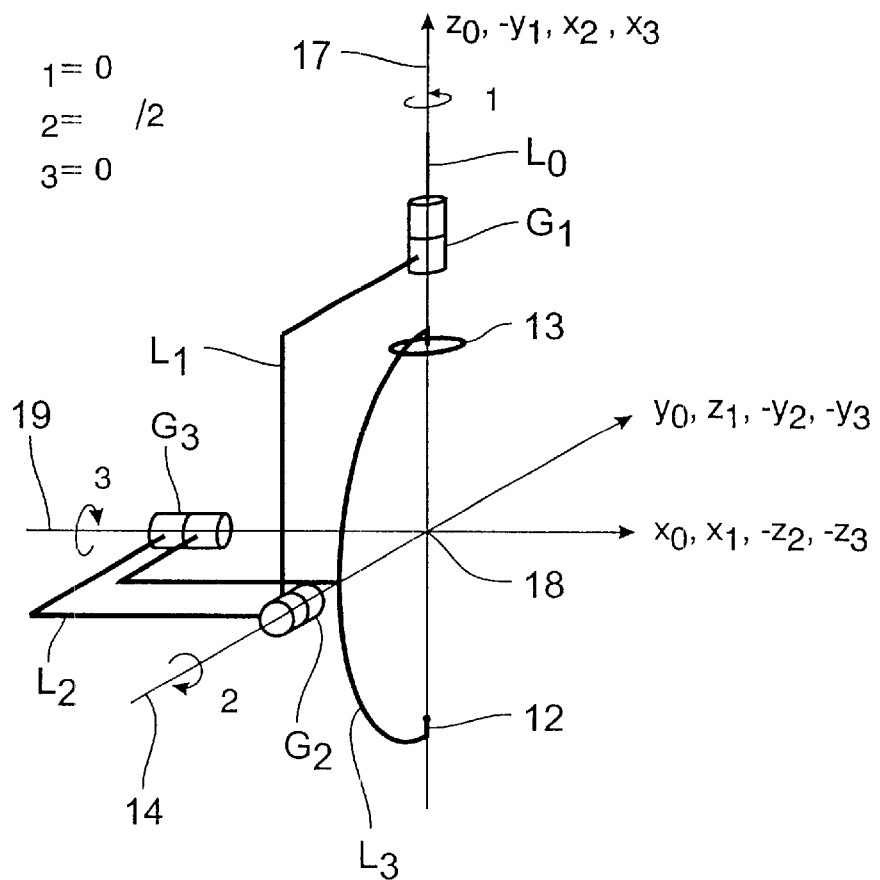
FIG. 6 is a diagrammatic view of the X-ray device shown in FIG. 5.

FIG. 6 is a diagrammatic representation of the first embodiment of the X-ray device in conformity with FIG. 5. Fixed mounts L therein are linked by way of pivot joints G as follows. The mount $L_0$ corresponds to the L-arm suspension and is attached, for example to the ceiling of the building. The mount $L_1$ is the L-arm (16 in FIG. 5). The mount $L_2$ is the C-arm suspension (22 in FIG. 5). The mount $L_3$ is the C-arm (11 in FIG. 5). The link $G_1$ connects the mounts $L_0$ and $L_1$. The link $G_2$ connects the mounts $L_1$ and $L_2$. The link $G_3$ connects the mounts $L_2$ and $L_3$. Each link defines one of the axes of rotation that intersect at the isocenter.

As is common practice in the field of robotics, a right-hand cartesian co-ordinate system $(x_k, y_k, z_k)$ is introduced with the mounts $L_k$ (for k=0, 1, 2, 3). These four co-ordinate systems move together with the mounts. The origin of all of said four co-ordinate systems is coincident with the isocenter 18 and the axes are oriented as shown in FIG. 6. The angle between the positive $x_{k-1}$ axis and the positive $x_k$ axis is referred to as $\theta_k$ (for k=1, 2, 3). Each of these angles can assume an arbitrary value within a predetermined angular range. Each $(\theta_1, \theta_2, \theta_3)$ triplet describes a configuration of the X-ray device shown. FIG. 6 shows the basic configuration that is characterized by the angles $\theta_1=0$, $\theta_2=-\pi/2$ and $\theta_3=0$. A point in space can be described by its co-ordinates $x_3=(x_3, y_3, z_3)$ in the co-ordinate system that is associated with the mount $L_3$, but also by its co-ordinates $x_2=(x_2, y_2, z_2)$, by its co-ordinates $x_1=(x_1, y_1, z_1)$ and by its co-ordinates $x_0=(x_0, y_0, z_0)$.

The transfer from one co-ordinate system to the next is described as follows by the matrix vector product:

$$x_{k-1} = R_k(\theta_k) x_k \text{ for } k=1,2,3$$

where $R_k(\theta_k)$ is a simple known rotation matrix.

When the angles $\theta_1$, $\theta_2$ and $\theta_3$ are varied, the X-ray source is moved approximately as a function of a real parameter s that covers an interval $[s_-, s_+]$. In study books on robotics it is demonstrated that the trajectory a(s) of the X-ray source for given angles $\theta_1(s)$, $\theta_2(s)$ and $\theta_3(s)$ can be calculated by means of the formula $$a(s) = R(\theta_1(s), \theta_2(s), \theta_3(s)) x_{src}, \ s \in [s_-, s_+]$$

Therein, $x_{src}$ is a vector and $R(\theta_1(s), \theta_2(s), \theta_3(s))$ is a rotation matrix. More specifically, $x_{src}=(-d_{src}, 0, 0)$ where $d_{src}$ denotes the distance between the X-ray source and the isocenter. The rotation matrix has the form $R(\theta_1, \theta_2, \theta_3) =$
| | | |
|---|---|---|
| $\cos\theta_1\cos\theta_2\cos\theta_3 - \sin\theta_1\sin\theta_3$ | $-\cos\theta_1\cos\theta_2\sin\theta_3 - \sin\theta_1\cos\theta_3$ | $\cos\theta_1\sin\theta_2$ |
| $\sin\theta_1\cos\theta_2\cos\theta_3 + \cos\theta_1\sin\theta_3$ | $-\sin\theta_1\cos\theta_2\sin\theta_3 + \cos\theta_1\cos\theta_3$ | $\sin\theta_1\sin\theta_2$ |
| $-\sin\theta_2\cos\theta_3$ | $\sin\theta_2\sin\theta_3$ | $\cos\theta_2$ |

Because the displacement of the X-ray source 12 along a trajectory can be realized exclusively by multiplication by a rotation matrix, the trajectory of the X-ray source 12 is situated on a spherical surface around the origin of the co-ordinate system, that is, around the isocenter 18.

The parameter s does not necessarily correspond to time. The trajectory can also be described by another parameter, that is, in as far as it follows from the parameter s by way of a parameter transformation. Parameter transformations are bijective continuous maps. The parameterization of the curve in time is realized by finding a suitable parameter transformation s(t). In order to describe a realistic movement of the X-ray source 12 along the trajectory in time t, the parameter transformation must also be differentiable. This is because the speed of the X-ray source 12 along the trajectory is nothing but the derivative of a(s) as a function of time.

Summarizing it is to be noted again that the C-arm 11 and the C-arm mount in the first embodiment of the X-ray device are rotatable simultaneously about the C-arm axis 19 and the propeller axis 14, respectively, by way of a motor and in a controlled fashion. During such rotation projection images of the object to be imaged can be acquired. It is important that the position of the X-ray source 12 along the trajectory is known for each projection image. Preferably, the propeller axis 14 of the first embodiment is conceived in such a manner that the C-arm 11 can be rotated about the propeller axis 14 through an angle of up to 270°, of up to 360° or through a multiple of 360°.

Describing the position of the X-ray source as above while utilizing a three-dimensional cartesian co-ordinate system that is arranged in the isocenter is not absolutely necessary. Every three-dimensional co-ordinate system, for example, a spherical co-ordinate system, is suitable to describe the position of the X-ray source 12. Furthermore, the same trajectory can be parameterized in different ways or be completed by the X-ray source 12 at a different speed.

The described formalism, however, enables all feasible trajectories to be described on a spherical surface. In accordance with the invention those trajectories are chosen for which at least two angles vary during the acquisition of the projection images. If only one angle were to vary, there would be obtained a planar trajectory that would be situated in a single plane and that would not lead to the completeness condition being satisfied. The described formalism can be realized directly by the X-ray device that is shown in the FIGS. 5 and 6 and also by the X-ray device that will be described in detail hereinafter with reference to the FIGS. 7 and 8; this is a particularly advantageous feature.

Figure 7:
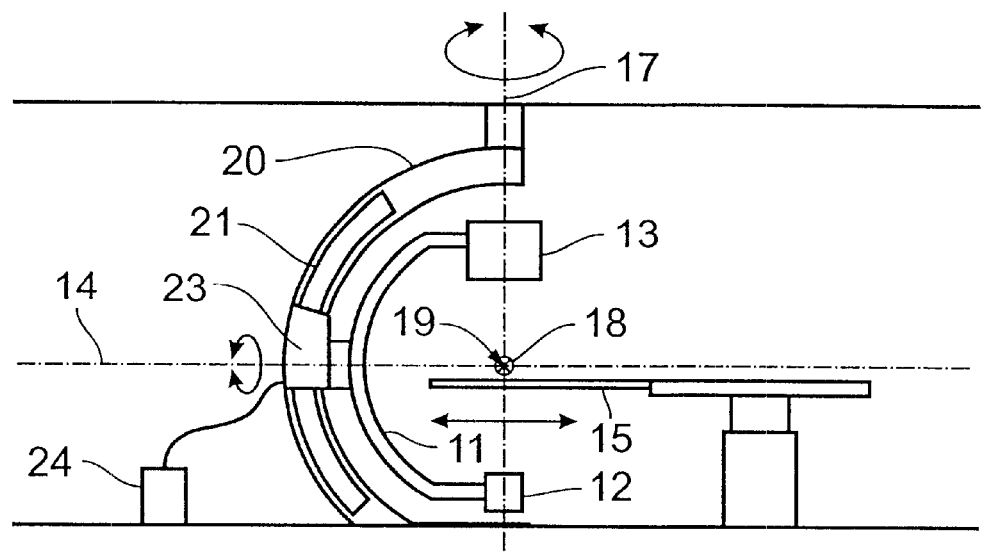
FIG. 7 is a side elevation of a second embodiment of an X-ray device in accordance with the invention.

FIG. 7 shows a further embodiment of an X-ray device in accordance with the invention. The reference numerals that are used in FIG. 7 denote the same characteristics as in FIG. 5. The C-arm axis 19 again extends perpendicularly to the plane of drawing and passes through the isocenter 18 in the Figure shown. The C-arm 11 is journaled by way of the C-arm mount 23 and is rotatable about the propeller axis 14 while the C-arm mount 23 is rotated at the same time about the C-arm axis 19 and projection images are acquired. This possibility already exists in the first embodiment of the X-ray device as shown in FIG. 5. The decisive difference with respect to the first embodiment, however, consists in that the propeller axis 14 also rotates in the case of rotation about the C-arm axis 19. Therefore, the propeller axis is not always horizontal. Moreover, the C-arm 11 can be constructed so as to be lighter, thus enabling faster movement of the propeller.

Figure 8:
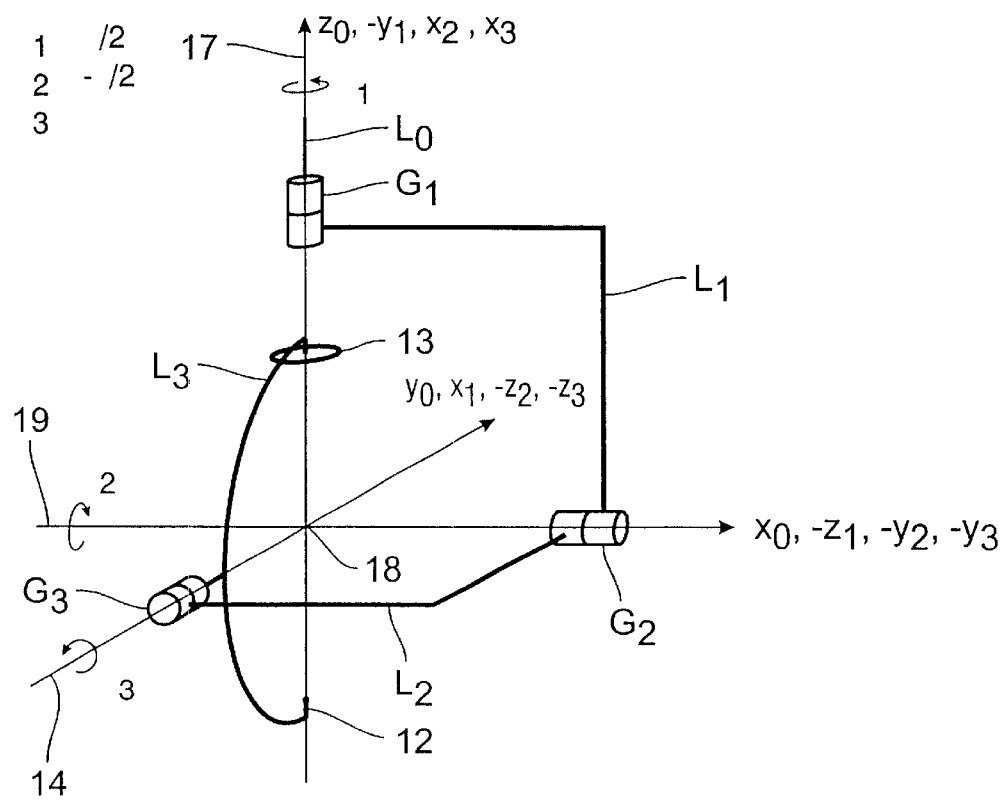
FIG. 8 is a diagrammatic view of the X-ray device that is shown in FIG. 7.

FIG. 8 is a diagrammatic representation of the second embodiment of the X-ray device. The co-ordinate systems that are linked to the mounts are chosen in such a manner that the same rotation matrix as used in the first embodiment can be employed so as to form an arbitrary trajectory that can be followed by the X-ray device. The position of the arm that is shown in FIG. 8 is characterized by the angles $\theta_1 = \pi/2$, $\theta_2 = -\pi/2$, $\theta_3 = 0$. The propeller angle of the X-ray device of the second embodiment can be varied preferably through 360° or through a multiple of 360°.

For the realization of the trajectories it is to be noted that the movement along a trajectory must commence with an acceleration phase and terminate with a deceleration phase. This can be achieved by way of a suitable parameter transformation s=s(t), that is, without the shape of the trajectory being changed. However, the period of time that is required to complete the trajectory is thus increased. Alternatively, the desired trajectory can be extended with acceleration and deceleration phases. The part of interest of the extended trajectory can then be completed at a more uniform speed.

The two angles of the trajectory that can be varied should be differentiable twice so that the trajectory can be physically realized. Preferably, the angles should even be continuously twice differentiable, so that discontinuous accelerations are avoided. The first derivatives of the angles can then serve to characterize the trajectories. A minimum number of changes of sign are desired for the derivatives. Approximately constant first derivatives are even better.

The adjustment ranges of the angles of rotation about the C-arm axis and the L-arm axis are limited to 180° or less for mechanical reasons. From a technical point of view it is easier to limit the angle of rotation for the propeller motion also to less than 360°. However, for closed trajectories it is desirable that the propeller motion can take place without restriction. This will usually necessitate the use of a slip ring for the transfer of electrical signals.

For the configuration of the trajectories care must be taken that the X-ray source, the X-ray detector and other parts of the examination device do not collide with the object to be examined or with its support, usually being a patient on the patient table.

The differences in the configuration of the embodiments of the X-ray device that are shown in the FIGS. 5 and 7 have consequences for the trajectories that can be followed in the case of a fixed position of the L-arm. The embodiments shown can also be varied in a sense that the L-arm is not constructed so as to be rotatable, is connected to the floor instead of to the ceiling, and is arranged on a displaceable carriage. Slip rings may be provided so as to realize the rotary movement around the propeller axis. In the embodiment that is shown in FIG. 5 the C-arm may also cover more than 180° and be rotated through more than 180° about the C-arm axis.

FIG. 9 shows a table that contains the angles of rotation $\theta_1(s)$, $\theta_2(s)$ and $\theta_3(s)$ for a first embodiment of the X-ray device in accordance with the invention and for a second embodiment of the X-ray device in accordance with the invention. The symbol sign stands for the sign function that is defined by sign [x]=+1 for $x \geq 0$ and sign [x]=-1 for x<0. Each of the trajectories shown in the FIGS. 10a to 19a is described by the corresponding angle of rotation $\theta_1(s)$, $\theta_2(s)$ and $\theta_3(s)$ when the parameter s completes the interval [0,1].

For the first embodiment of an X-ray device in accordance with the invention the angle $\theta_2(s)$ is associated with the propeller axis and the angle $\theta_3(s)$ is associated with the C-arm axis. For the second embodiment of an X-ray device in accordance with the invention the angle $\theta_2(s)$ is associated with the C-arm axis and the angle $\theta_3(s)$ is associated with the propeller axis. The angle $\theta_1$ indicates the position of the L-arm and remains constant during the acquisition of the cone beam projections.

Mainly the alternative versions of the trajectory that are valid for the first embodiment of the X-ray device in accordance with the invention will be elaborated upon hereinafter. The trajectories that are valid for the second embodiment of the X-ray device are usually identical, be it that many trajectories are valid only for the first embodiment.

The trajectories that are given by way of example are also dependent on given additive and multiplicative constants. These constants, if necessary, have to be chosen so that the completeness condition is satisfied. For these examples of trajectories the distance between the X-ray source and the isocenter is 660 mm and the radius of the examination zone amounts to approximately 120 mm. Furthermore, the constants are chosen to be such that the completeness condition is satisfied each time for this examination zone.

The trajectories in the FIGS. 10a to 19d are shown in a cartesian co-ordinate system whose axes are denoted by the references $x_0$, $y_0$, $z_0$ and correspond to the axes $x_0$, $y_0$, $z_0$ in the FIGS. 6 and 8. The trajectories are situated each time on a spherical surface whose center is situated at the origin of the co-ordinate system. The trajectories shown enclose each time an examination zone that is to be imaged and is situated at the origin of the co-ordinate system. Furthermore, the trajectories that are shown in the FIGS. 10 to 19d are calculated, while utilizing the angles that are given in FIG. 9 and the formula $a(s)=R(\theta_1(s), \theta_2(s), \theta_3(s)) x_{src}$ for a given number of values of the parameter s that are uniformly distributed across the interval $\{0,1\}$. The trajectories are three-dimensional curves, because the angles of rotation $\theta_2$ and $\theta_3$ also change when the parameter s is changed. The trajectories that are shown in the FIGS. 10a to 19d all satisfy the completeness conditions for a spherical examination zone that has a radius of approximately 120 mm.

Figure 10A:
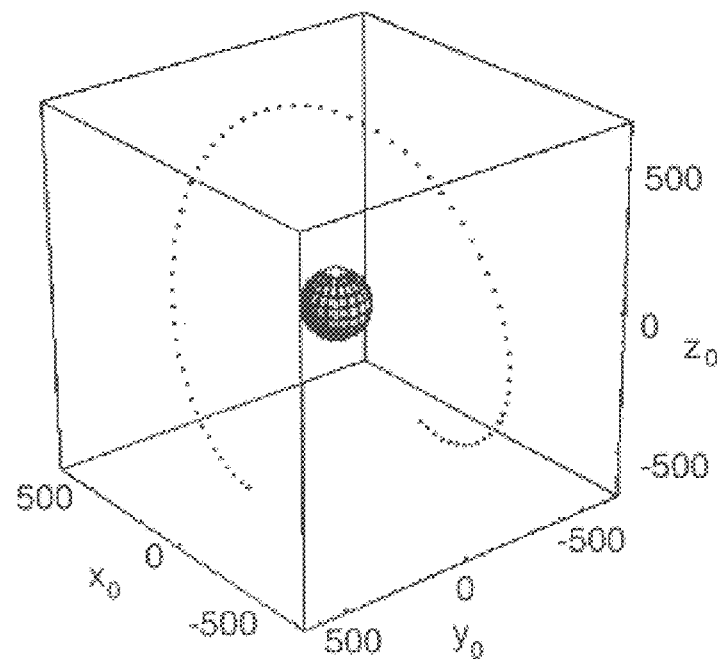
FIGS. 10a, 10b show in perspective a trajectory in accordance with the invention, representing a first spherical spiral, and the associated spherical caps of the trajectory.
Figure 10B:
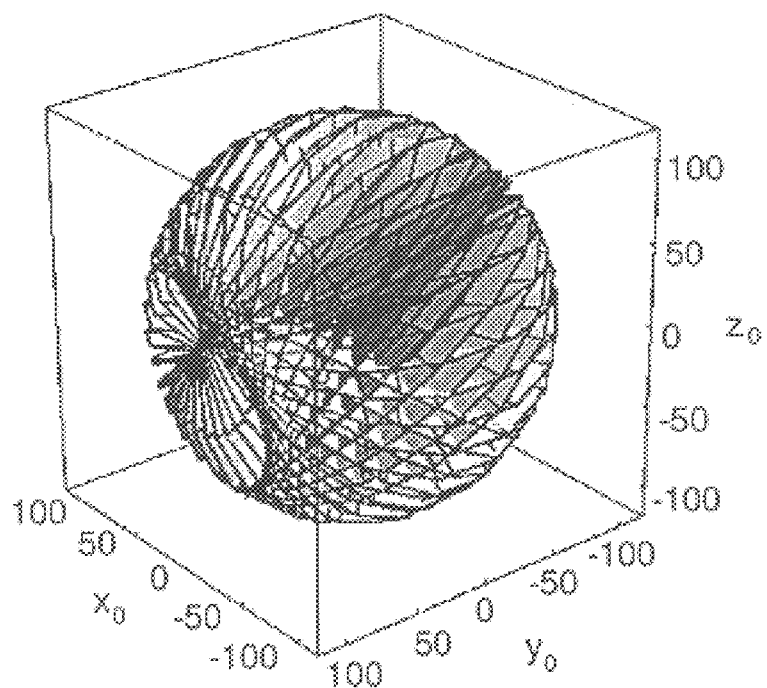
Figure 11A:
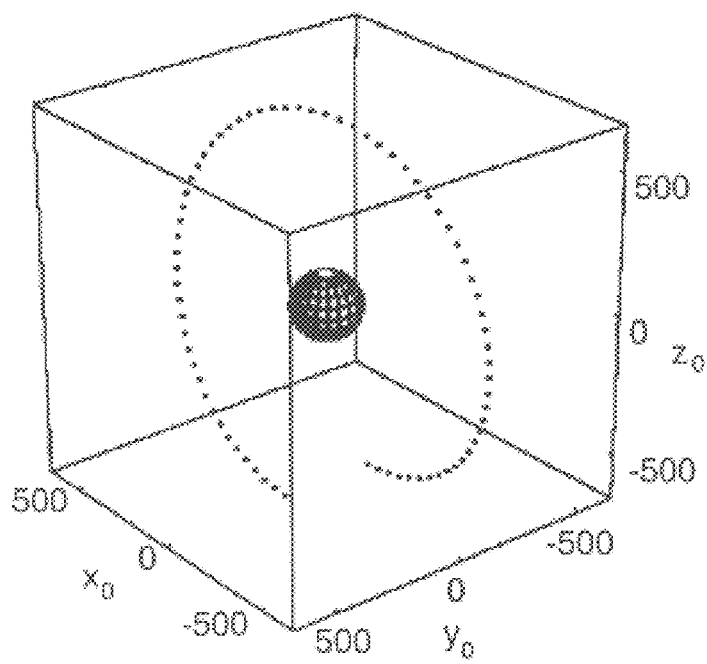
FIGS. 11a to 11e show a trajectory in accordance with the invention that represents a second spherical spiral, the associated spherical caps of the trajectory and three side elevations of the trajectory.
Figure 11B:
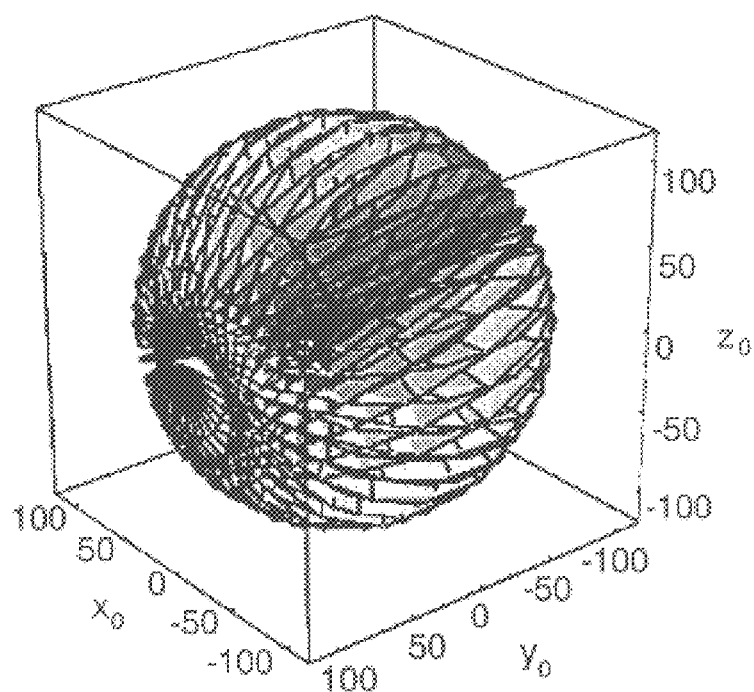
Figure 12A:
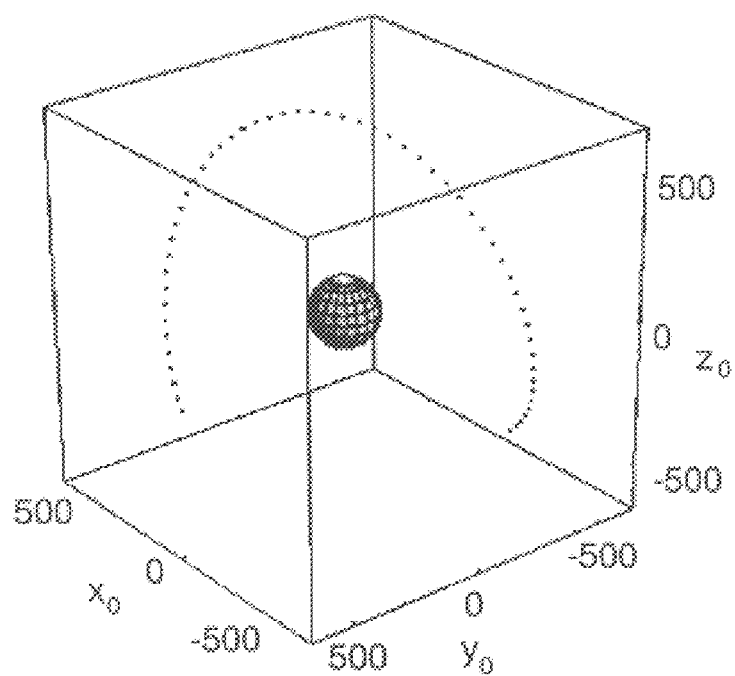
FIGS. 12a, 12b show in perspective a trajectory in accordance with the invention that represents a ¾ spherical spiral, and the associated spherical caps of the trajectory.
Figure 12B:
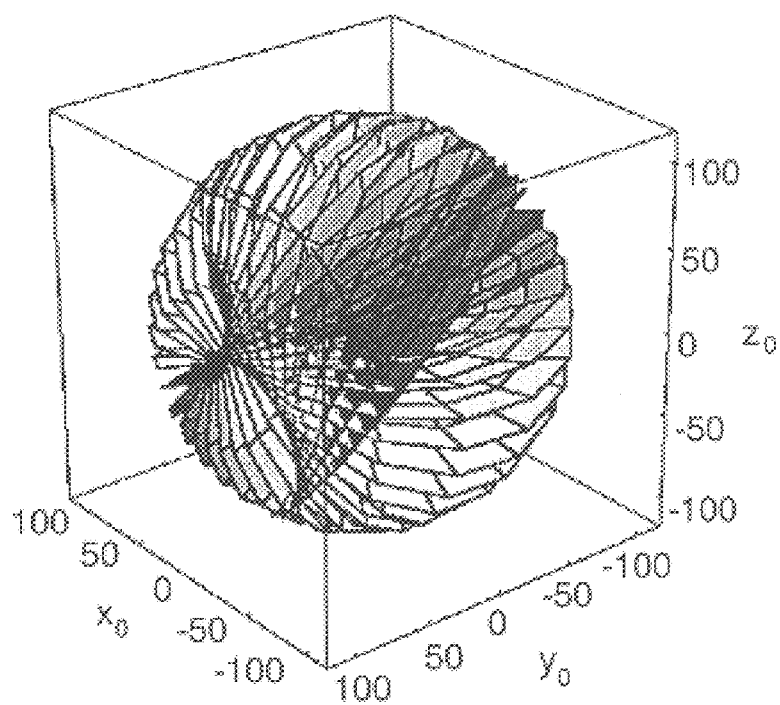
Figure 13A:
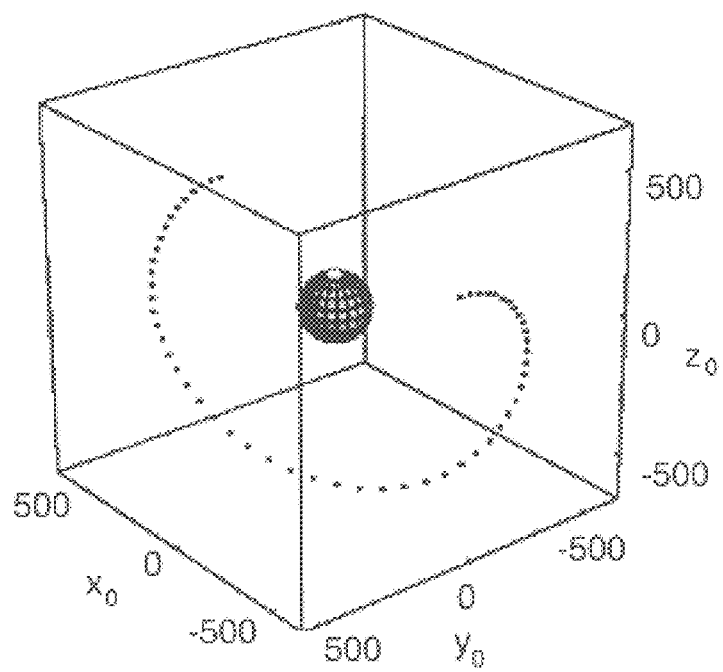
FIGS. 13a to 13e show a trajectory in accordance with the invention that represents a half, bent eight, the associated spherical caps of the trajectory and three side elevations of the trajectory.
Figure 13B:
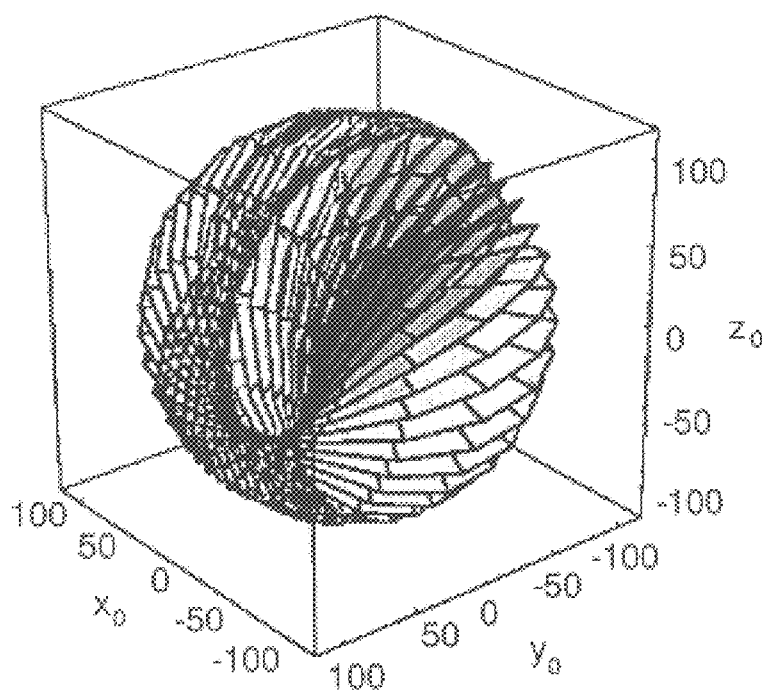

The FIGS. 10a, 11a and 12a show trajectories that represent different configurations of a spherical spiral. They essentially resemble a coil-like curve that is projected onto a spherical surface. FIG. 13a shows a trajectory that looks like a half figure eight that is arranged on a spherical surface. It is a characteristic aspect of all of such trajectories that the derivatives of both angles of rotation do not exhibit a change of sign. The FIGS. 10b, 11b, 12b and 13b show the filling of the examination zone with spherical caps that are associated with the respective trajectories. It appears that each of the trajectories shown in the FIGS. 10a, 11a, 12a and 13a satisfies the completeness condition, because the corresponding spherical caps would fill the examination zone without voids as their number increases.

Figure 11C:
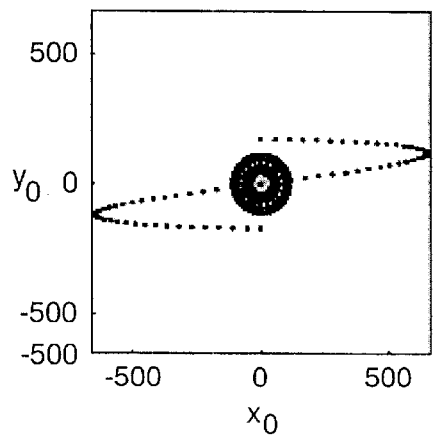
Figure 11D:
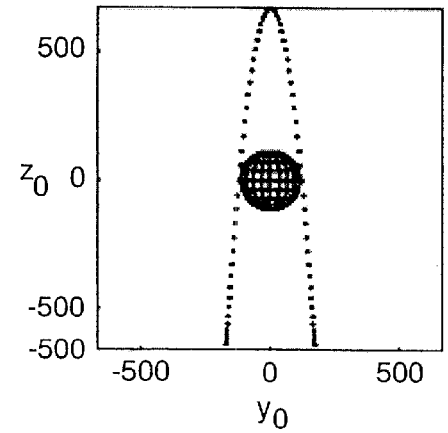
Figure 11E:
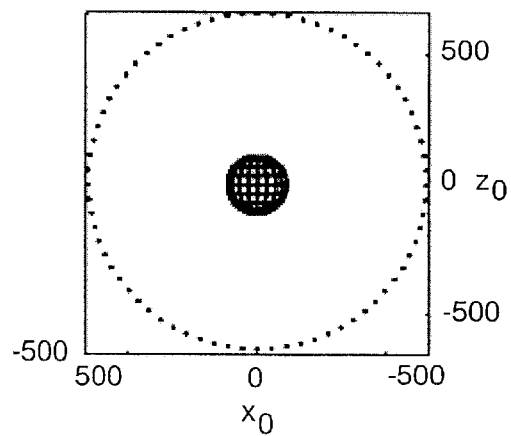

The FIGS. 11c, 11d and 11e show the course of the trajectory of FIG. 11a from a different viewing direction. Viewed from the $y_0$ direction, the trajectory appears as a closed circle in FIG. 11e. The X-ray source that is displaced along this trajectory, consequently, performs a rotation of 360° about the z axis. FIG. 11c shows the appearance of the trajectory when viewed from the $z_0$ direction. When the X-ray source is displaced in the direction of the y axis, it is at the same time displaced in the direction of the x axis, that is, first towards negative x values and subsequently towards positive x values. The course of the trajectory of FIG. 11a, as viewed from the $x_0$ direction, is shown in FIG. 11d. The helical trajectory that is shown in FIG. 12a is distinct from the helical trajectories that are shown in the FIGS. 10a and 11a in that the X-ray source that is displaced along the trajectory does not undergo a complete rotation about the z axis. When viewed from the x-z plane, the trajectory that is shown in FIG. 12a does not appear as a complete circle but as a ¾ circle.

Figure 13C:
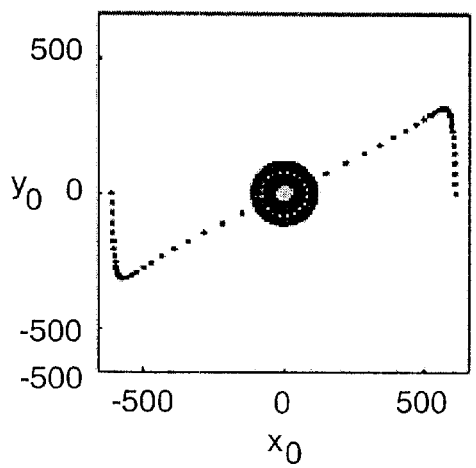
Figure 13D:
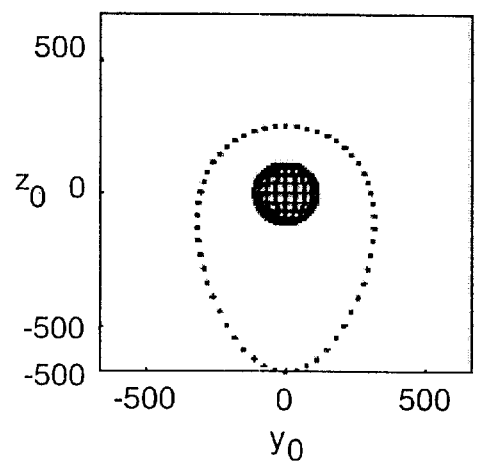
Figure 13E:
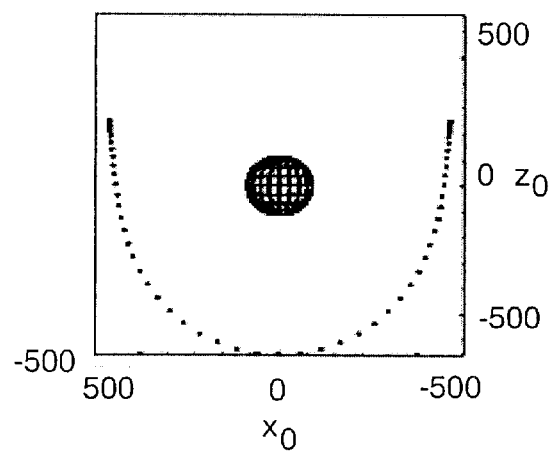

The FIGS. 13c, 13d and 13e show the course of the trajectory of FIG. 13a, that is, again from the three viewing directions along the $z_0$ axis, the $x_0$ axis and the $y_0$ axis so as to enable simpler representation of the course of the trajectory.

Figure 14A:
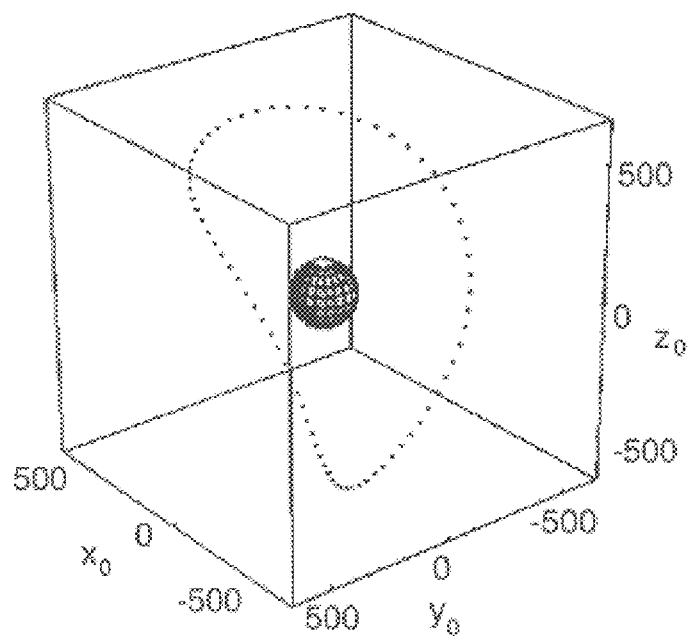
FIGS. 14a, 14b show in perspective a trajectory in accordance with the invention that represents a first bent circle, and the associated spherical caps of the trajectory.
Figure 14B:
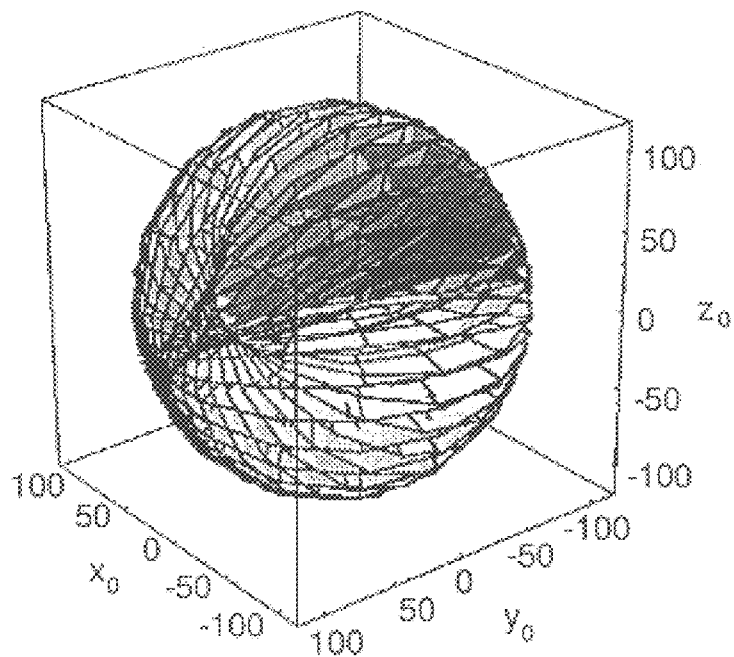
Figure 15A:
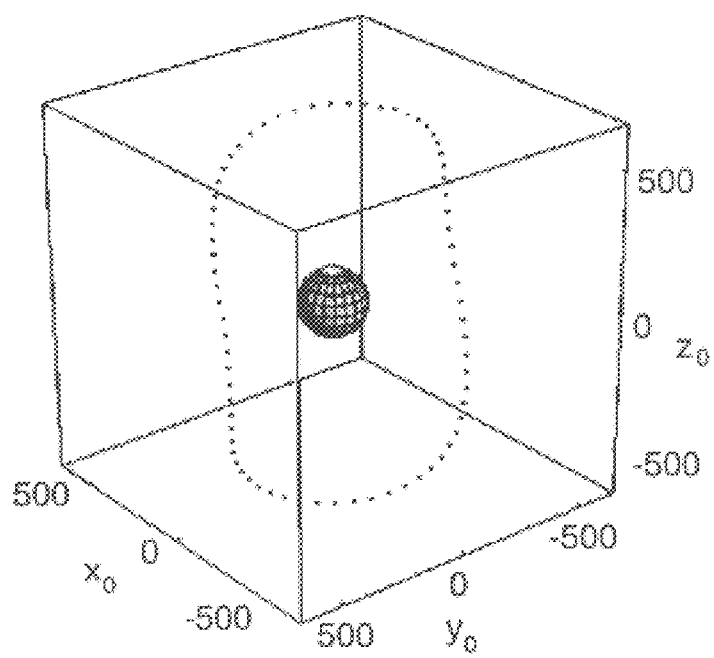
FIGS. 15a, 15b show in perspective a trajectory in accordance with the invention that represents a second curved circle, and the associated spherical caps of the trajectory.
Figure 15B:
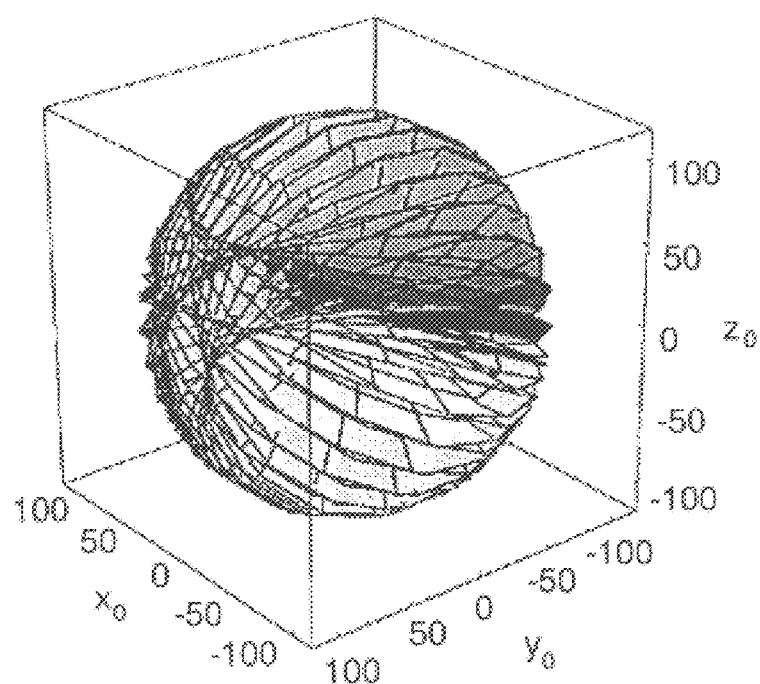

FIG. 14a and FIG. 15a show trajectories in accordance with the invention, each of which represents a bent circle that is situated on a spherical surface. These trajectories are characterized by a rotation through 360°, without a change of sign of the first derivative, about one of the axes and by a periodic movement with a change of sign about the other axis. The FIGS. 14b and 15b show the filling of the examination zone with spherical caps in conformity with the foregoing trajectories. Evidently, both trajectories satisfy the completeness condition. Moreover, they form closed curves so that an X-ray source can complete these trajectories a number of times in succession without stopping. The realization of these trajectories can be explained on the basis of the formulae for the angles of rotation that are given in FIG. 9. In conformity therewith an angle of rotation is increased by each time $2\pi$, because one of the angles of rotation is always a function of $2\pi s$, where s covers the range of values from 0 to 1. Furthermore, another angle of rotation is a periodic function, that is, in such a manner that the value of this angle becomes the same again after having traversed the value range of s. For the present trajectories trigonometric functions were used to describe the second angle of rotation.

Figure 16A:
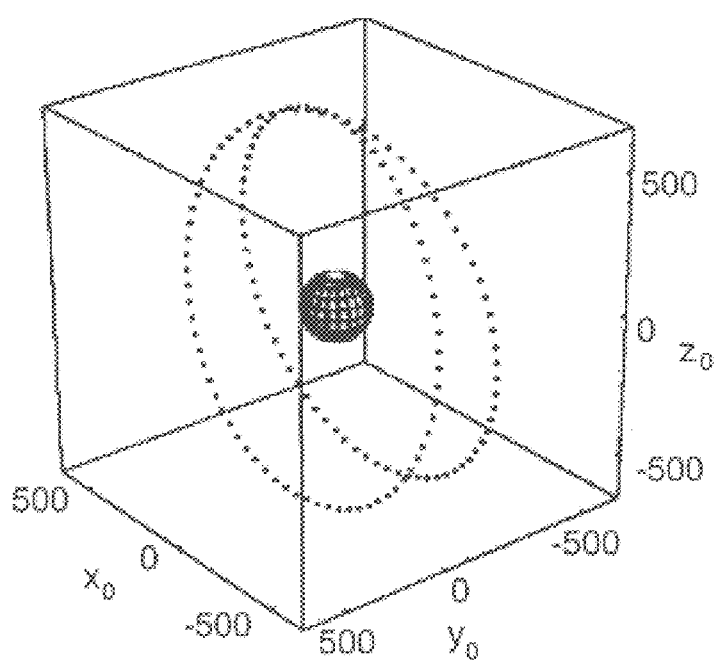
FIGS. 16a to 16e show a trajectory in accordance with the invention that represents two linked spherical spirals, the associated spherical caps of the trajectory, and three side elevations of the trajectory.
Figure 16B:
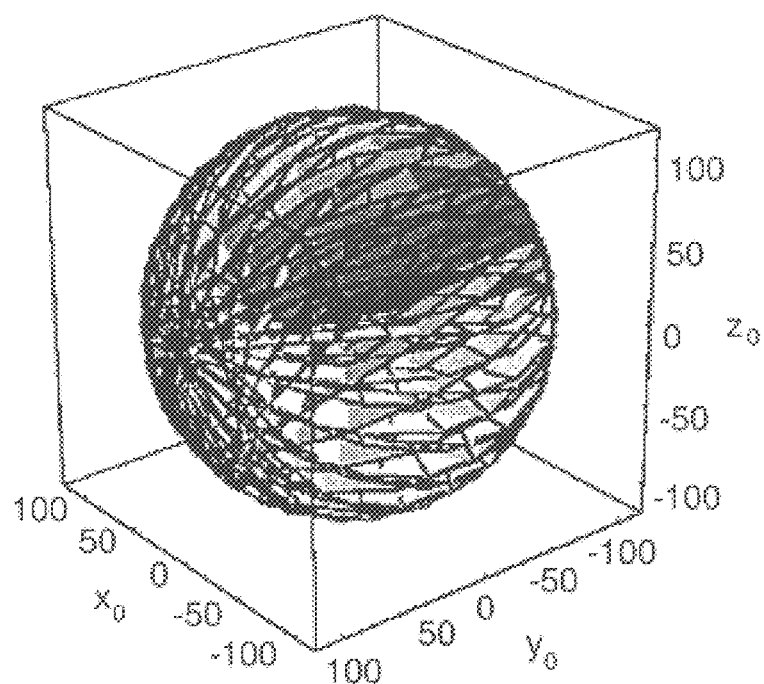
Figure 16C:
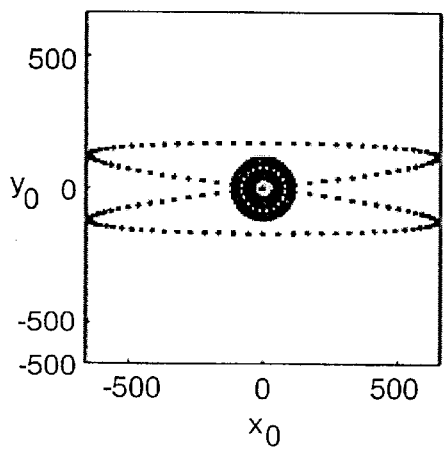
Figure 16D:
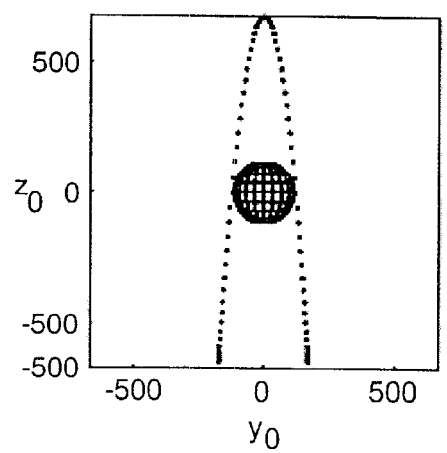
Figure 16E:
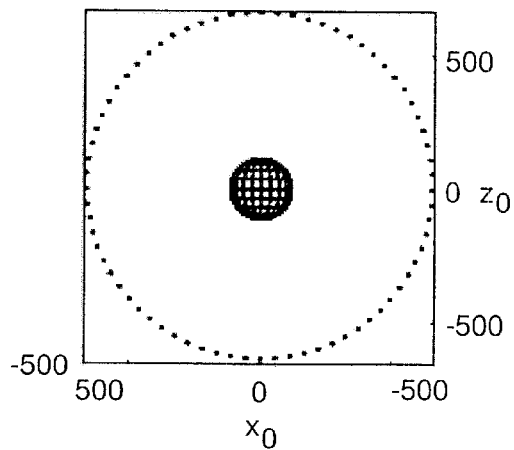

FIG. 16a shows a trajectory that is realized by linking two spherical spirals of the type shown in FIG. 11a. FIG. 16b shows that this trajectory is also complete. The advantage of this trajectory resides in the fact that it is closed and that it can be realized with small acceleration forces. The FIGS. 16c, 16d and 16e again show the trajectory of FIG. 16a from different viewing directions. Notably a comparison of the FIGS. 16c and 11c can be useful. When the curve that is shown in FIG. 11c is mirrored relative to the $y_0$ axis, so that all points that were situated to the right of the $y_0$ axis before are now situated to the left of the $y_0$ axis and vice versa, a further spherical spiral is obtained. When these two trajectories are joined, the trajectory shown in FIG. 16c is obtained.

Figure 17A:
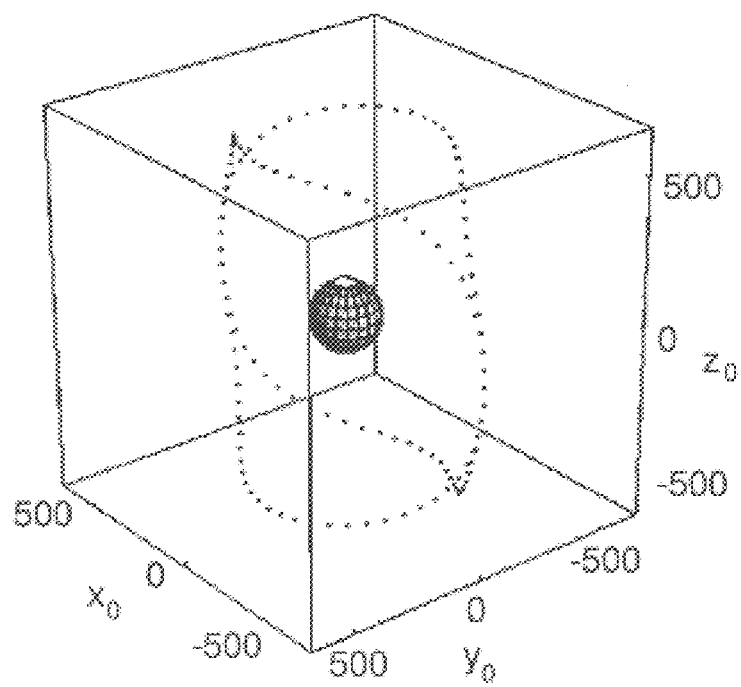
FIGS. 17a, 17b show in perspective a trajectory in accordance with the invention that represents two linked, bent circles, and the associated spherical caps of the trajectory.
Figure 17B:
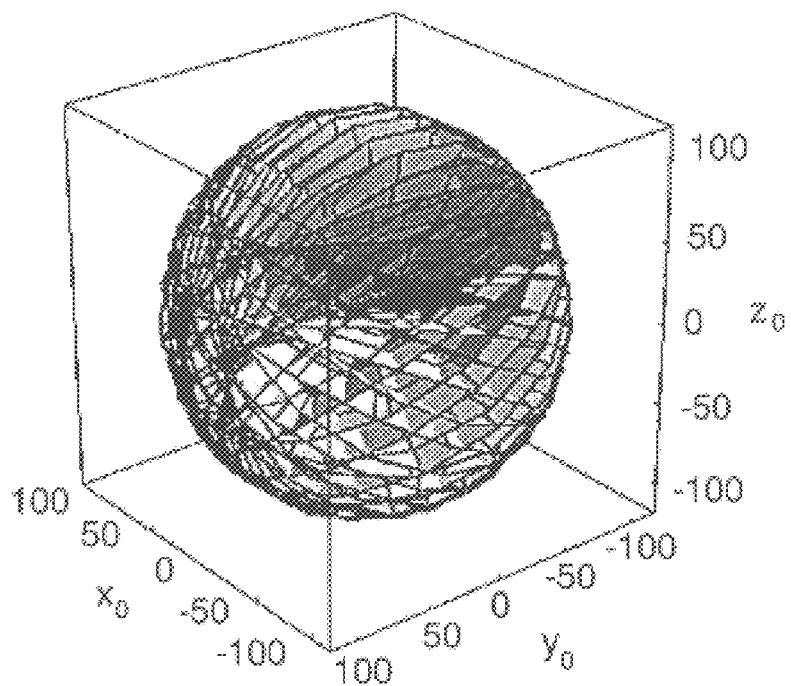

FIG. 17a shows a trajectory that is formed by the linking of two bent circles.

FIG. 17b again shows the filling of the examination zone with spherical caps. It appears that this trajectory also satisfies the completeness condition. Such linking offers the advantage of a symmetrical trajectory that may be advantageous for some reconstruction algorithms. The acceleration forces, however, are then slightly greater than for the trajectory shown in FIG. 16a.

Figure 18A:
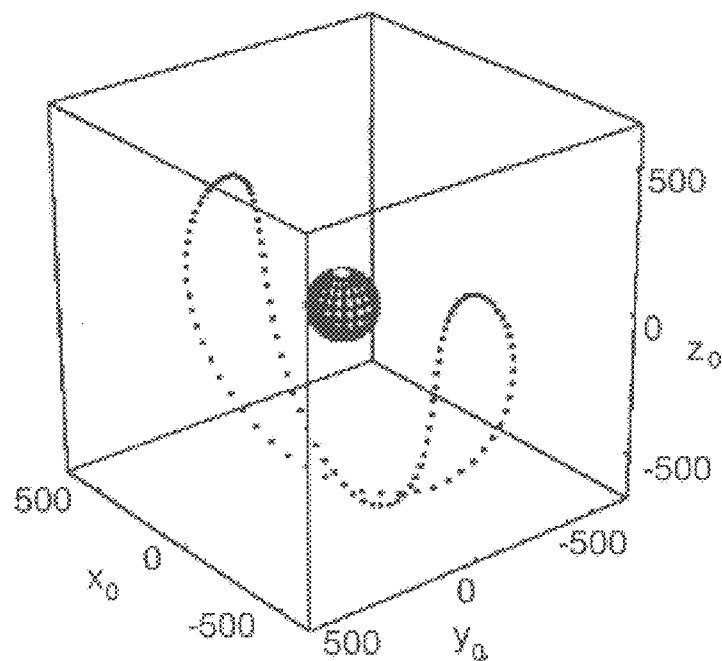
FIGS. 18a to 18e show in perspective a trajectory in accordance with the invention that represents a bent eight, the associated spherical caps of the trajectory, and three side elevations of the trajectory.
Figure 18B:
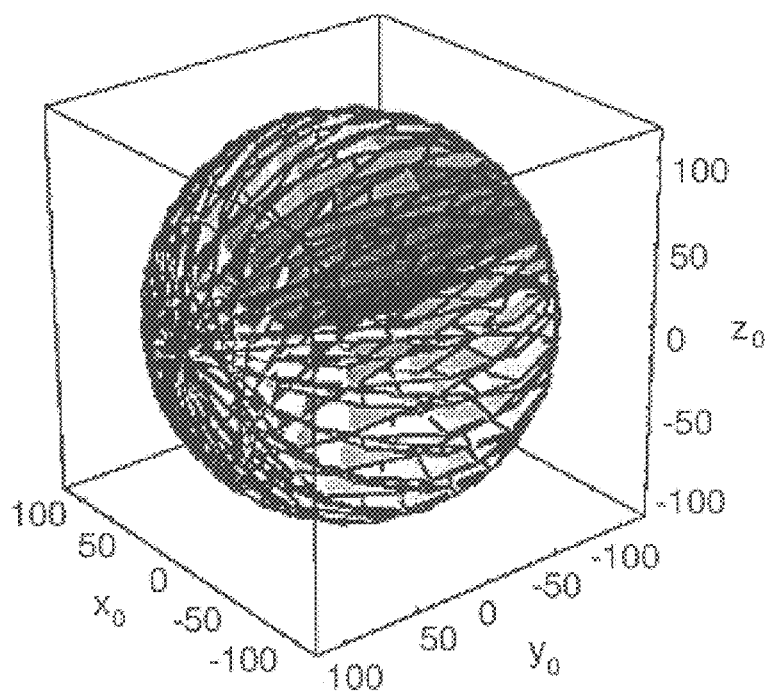
Figure 18C:
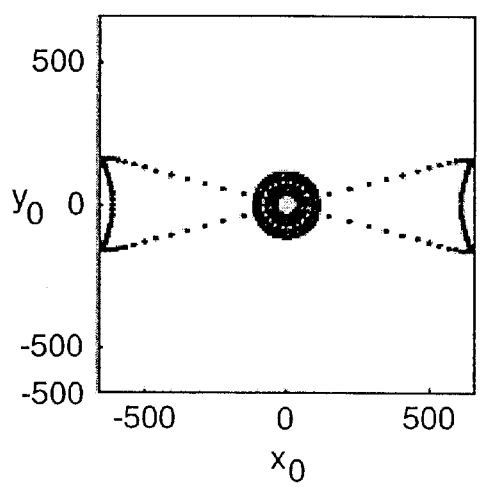
Figure 18D:
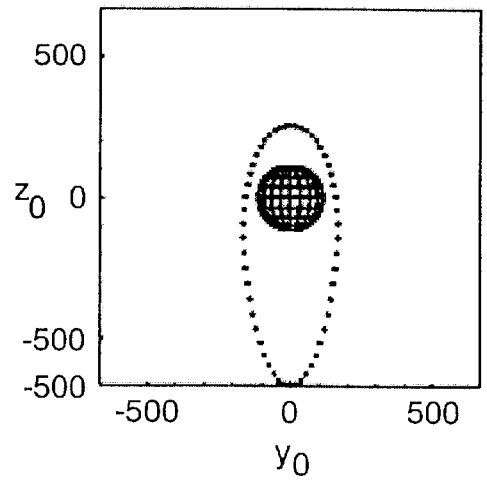
Figure 18E:
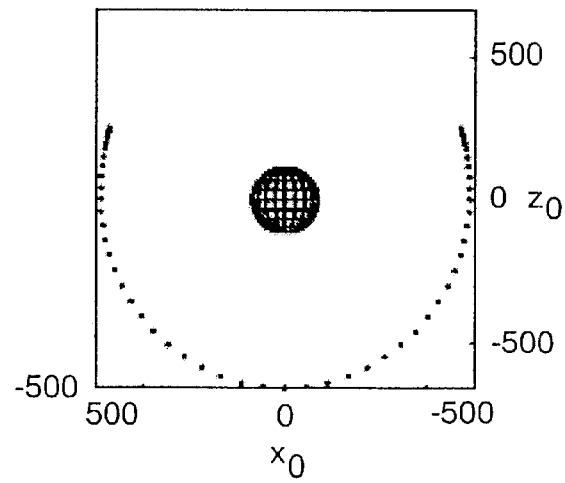

FIG. 18a shows a trajectory that corresponds to a figure eight that is positioned on a sphere. The trajectory thus constitutes a closed curve with two loops that are arranged opposite one another and may be considered to be a combination of two half figures eight as shown in FIG. 13a. The exact description of this curve is given by the functions stated in FIG. 9. FIG. 18b again confirms that the trajectory of FIG. 18a satisfies the completeness condition. The FIGS. 18c, 18d and 18e again show the course of the trajectory of FIG. 18a as viewed from three different viewing directions. The appearance of the trajectory as seen from the $z_0$ direction in FIG. 18c justifies the representation of a figure eight that is situated on a spherical surface. A left loop and a right loop can be seen. The common point of the oppositely situated loops is formed by the lowermost point in FIG. 18d and FIG. 18e. The oppositely situated loops of the figure eight are represented by the points that are shown to the right and to the left of the foregoing point. When viewed from this direction, an X-ray source that follows the trajectory would move, for example, from the uppermost right-hand point to the origin and then to the uppermost left-hand point and back again. Such a trajectory can be realized by means of the X-ray device of FIG. 5 without the use of a slip ring being necessary.

Figure 19A:
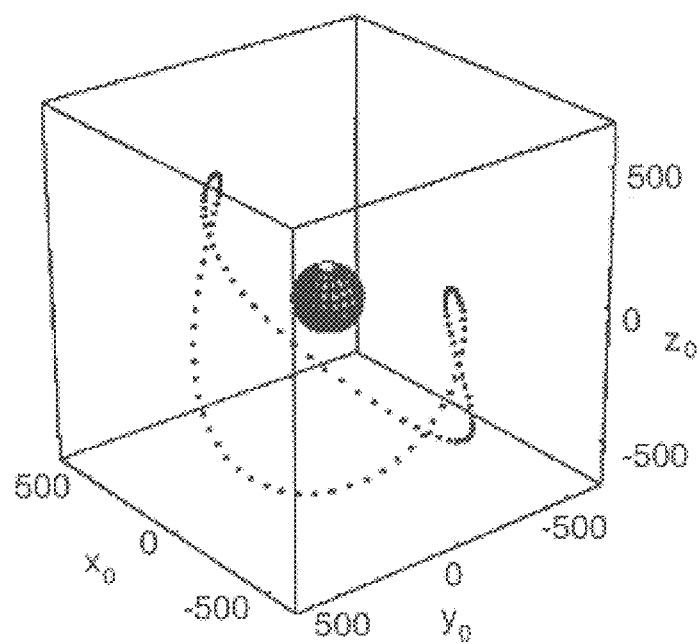
FIGS. 19a, 19b show a trajectory in accordance with the invention that represents a bent, double loop, and the associated spherical caps of the trajectory.
Figure 19B:
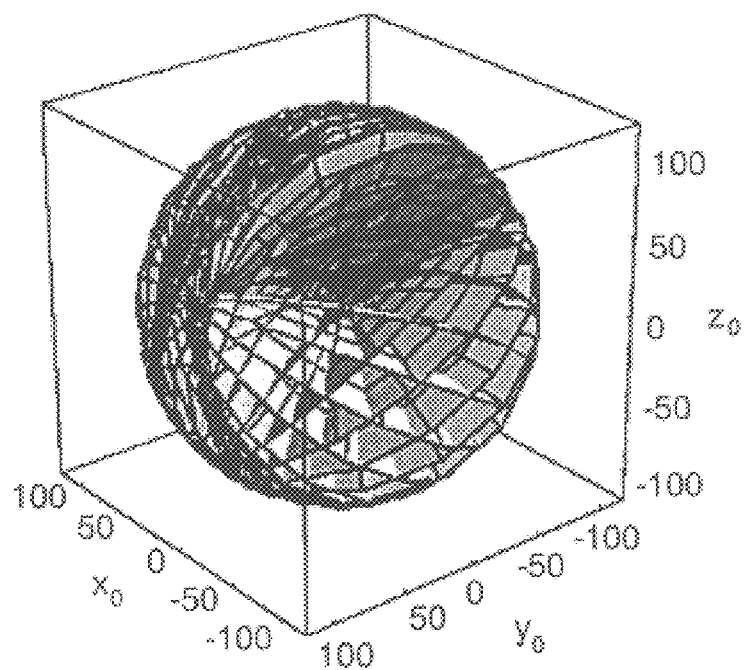

FIG. 19a shows a further version of a trajectory in accordance with the invention. FIG. 19b shows that this trajectory also satisfies the completeness condition. However, this trajectory can be realized only by means of the embodiment of the X-ray device that is shown in FIG. 5. The L-arm then extends laterally $(\theta_1(s)=-\pi/2)$. This trajectory thus also enables the formation of images of the lower part of the body and the legs of a patient. For all other trajectories, however, the L-arm is situated at the head or in the vicinity of the head of a patient; therefore, only the head and the torso can be imaged when these trajectories are used.

However, for the double loop the angle $\theta_2$ (rotation about the C-arm axis) must cover a range of approximately 225°; this can be realized by increasing the length of the supporting rail.

The invention provides trajectories for the acquisition of an as complete as possible set of projection images, notably of cone beam projections, of an object to be examined that is arranged in an examination zone. The trajectories shown are examples in this respect. An arbitrary number of other examples that are capable of satisfying the completeness condition, however, are likewise feasible. Moreover, the X-ray devices shown are merely examples that are suitable to realize the trajectories in accordance with the invention. The X-ray devices, however, can in principle also have a different construction and they need not necessarily be provided with a C-arm either.

What is claimed is:

1. A method for the acquisition of a set of projection images for the reconstruction of a three-dimensional image data set of an object to be examined that is arranged in an examination zone, said acquisition being performed by way of an X-ray device that includes an X-ray source and an X-ray detector, the X-ray source being displaced along a trajectory around the object to be examined, said trajectory being situated essentially on a spherical surface, in order to acquire the projection images, wherein the trajectory is configured in such a manner that the X-ray source can continuously follow the trajectory in one operation in order to acquire the set of projection images and wherein not all points of the trajectory are situated in a common plane.

2. The method as claimed in claim 1, wherein the trajectory is configured in such a manner that each plane that intersects the examination zone contains at least one point of the trajectory.

3. The method as claimed in claim 1, wherein the trajectory represents a closed curve.

4. The method as claimed in claim 1, wherein the trajectory represents a twice differentiable curve.

5. The method as claimed in claim 1, wherein the trajectory can be written in the form $$a(s) = R(\theta_1(s), \theta_2(s), \theta_3(s)) x_{src}$$

where $\theta_1(s)$, $\theta_2(s)$ and $\theta_3(s)$ are real functions of a real parameter s that are twice differentiable, $x_{src}$ is given by the distance $d_{src}$ between the X-ray source and the center of the spherical surface in conformity with $x_{src} = (-d_{src}, 0, 0)$, $R(\theta_1(s), \theta_2(s), \theta_3(s))$ is the rotation matrix:

$$R(\theta_{74}, \theta_2, \theta_3) = \begin{pmatrix} \cos\theta_1\cos\theta_2\cos\theta_3 - \sin\theta_1\sin\theta_3 & -\cos\theta_1\cos\theta_2\sin\theta_3 - \sin\theta_1\cos\theta_3 & \cos\theta_1\sin\theta_2 \\ \sin\theta_1\cos\theta_2\cos\theta_3 + \cos\theta_1\sin\theta_3 & -\sin\theta_1\cos\theta_2\sin\theta_3 + \cos\theta_1\cos\theta_3 & \sin\theta_1\sin\theta_2 \\ -\sin\theta_2\cos\theta_3 & \sin\theta_2\sin\theta_3 & \cos\theta_2 \end{pmatrix}$$

and a(s) is the position vector of the trajectory in relation to a right-hand cartesian co-ordinate system whose origin corresponds to the center of the spherical surface, wherein at least two of the functions $\theta_1(s)$, $\theta_2(s)$ and $\theta_3(s)$ are not constant, and wherein the trajectory a(s) is configured in such a manner that each plane that intersects the examination zone also intersects the trajectory.

6. The method as claimed in claim 5, wherein the function $\theta_3(s)$ is chosen so as to be constant.

7. The method as claimed in claim 5, wherein the first derivatives of the functions $\theta_1(s)$ and $\theta_2(s)$ do not exhibit a change of sign.

8. The method as claimed in claim 7, wherein the functions $\theta_1(s)$ and $\theta_2(s)$ are chosen to be such that one of their first derivatives does not exhibit a change of sign and that the other derivative exhibits at least one change of sign.

9. The method as claimed in claim 7, wherein the functions $\theta_1(s)$ and $\theta_2(s)$ are chosen to be such that their first derivatives exhibit each time at least one change of sign.

10. The method as claimed in claim 1, wherein the projection images are cone beam projections.

11. An X-ray device for the acquisition of a set of projection images for the reconstruction of a 3D image data set of an object to be examined that is arranged in an examination zone, said X-ray device comprising: an X-ray source; an X-ray detector for the acquisition of the projection images of the object to be examined; and a control unit for guiding the X-ray source along a trajectory around the object to be examined, said trajectory being situated essentially on a spherical surface, in order to acquire the projection images, wherein said X-ray device is constructed in such a manner that the X-ray source can continuously follow the trajectory in one operation in order to acquire the set of projection images and wherein not all points of the trajectory are situated in a common plane.

12. The X-ray device as claimed in claim 11, wherein said X-ray device is a C-arm system that includes a C-arm that is supported by a C-arm mount.

13. The X-ray device as claimed in claim 12, further wherein the C-arm and the C-arm mount are simultaneously rotatable about a C-arm axis and a propeller axis, respectively, the propeller axis and the C-arm axis being orthogonal to one another and intersecting one another in an isocenter.

14. The X-ray device as claimed in claim 12, wherein the propeller axis and the C-arm are situated essentially in a common plane.

15. The X-ray device as claimed in claim 12, wherein the propeller axis remains the same upon rotation of the C-arm about the C-arm axis.

16. The X-ray device as claimed in claim 11, wherein said X-ray device is arranged for the acquisition of cone beam projections.

17. The X-ray device as claimed in claim 11, wherein the rotation about the propeller axis may amount to a multiple of 360°.

* * * * *